United States Patent
Frisby et al.

(10) Patent No.: US 12,364,613 B2
(45) Date of Patent: Jul. 22, 2025

(54) HYDRAULIC CRIMPING DEVICE

(71) Applicant: Medtronic Vascular, Inc., Santa Rosa, CA (US)

(72) Inventors: Paraic Frisby, Galway (IE); Eveanne Slattery, Dublin (IE); John Gallagher, Parkmore Business Park West (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 18/614,699

(22) Filed: Mar. 24, 2024

(65) Prior Publication Data

US 2024/0225830 A1   Jul. 11, 2024

Related U.S. Application Data

(62) Division of application No. 17/124,021, filed on Dec. 16, 2020, now Pat. No. 11,974,917.

(Continued)

(51) Int. Cl.
*A61F 2/95* (2013.01)
*A61F 2/24* (2006.01)
(Continued)

(52) U.S. Cl.
CPC .......... *A61F 2/9525* (2020.05); *A61F 2/2427* (2013.01); *A61F 2/24* (2013.01); *A61M 5/3135* (2013.01); *A61M 5/31511* (2013.01)

(58) Field of Classification Search
CPC .... A61F 2/9522; A61F 2/9525; B23P 11/005; A61M 5/3135; A61M 5/31511–31513
See application file for complete search history.

(56) References Cited

U.S. PATENT DOCUMENTS 1,948,388 A * 2/1934 Liberson ............ A61B 17/3401
604/191
5,992,000 A   11/1999 Humphrey et al.
(Continued)

FOREIGN PATENT DOCUMENTS

AU       1472599 A      9/1999
DE    10212707 A1    10/2003
(Continued)

OTHER PUBLICATIONS

Written Opinion and International Search Report dated Apr. 14, 2021 in International Appln. No. PCT/US2020/065613.
(Continued)

*Primary Examiner* — Matthew P Travers
(74) *Attorney, Agent, or Firm* — Medler Ferro Woodhouse & Mills PLLC

(57) ABSTRACT

A crimping device for reducing the size of prosthetic heart valve devices and other medical devices. A hydraulically operated piston advances a pusher toward an opening of a funnel. An interior surface of the funnel is configured to provide substantially uniform compression forces to a prosthetic heart valve device between the pusher and the funnel as the pusher advances the prosthetic heart valve device into the funnel. A system may comprise the crimping device and a prosthetic heart valve device positioned between the pusher and the funnel. A technique for using the crimping device includes delivering a pressurized fluid and crimping a prosthetic heart valve device using the interior surface of the funnel.

17 Claims, 16 Drawing Sheets

Related U.S. Application Data

(60) Provisional application No. 62/951,918, filed on Dec. 20, 2019.

(51) Int. Cl.
*A61M 5/31* (2006.01)
*A61M 5/315* (2006.01)

(56) References Cited

U.S. PATENT DOCUMENTS

| | | |
|---|---|---|
| 6,009,614 A | 1/2000 | Morales |
| 6,068,635 A | 5/2000 | Gianotti |
| 6,471,718 B1 | 10/2002 | Staehle et al. |
| 8,100,959 B2 | 1/2012 | Que et al. |
| 2003/0225445 A1 | 12/2003 | Derus et al. |
| 2007/0162100 A1 | 7/2007 | Gabbay |
| 2007/0239271 A1 | 10/2007 | Nguyen |
| 2008/0071362 A1 | 3/2008 | Tuval et al. |
| 2010/0049313 A1 | 2/2010 | Alon et al. |
| 2010/0057185 A1 | 3/2010 | Melsheimer et al. |
| 2011/0208296 A1 | 8/2011 | Duffy et al. |
| 2011/0224678 A1 | 9/2011 | Gabbay |
| 2011/0295216 A1 | 12/2011 | Miller |
| 2012/0083874 A1 | 4/2012 | Dale et al. |
| 2012/0330408 A1 | 12/2012 | Hillukka et al. |
| 2015/0135647 A1 | 5/2015 | Dale et al. |

FOREIGN PATENT DOCUMENTS

| | | |
|---|---|---|
| WO | 9959503 A1 | 11/1999 |
| WO | 2003079933 A1 | 10/2003 |
| WO | 2010096176 A1 | 8/2010 |
| WO | 2012023979 A2 | 2/2012 |

OTHER PUBLICATIONS

Notice on the First Office Action, Chinese Application No. 202080084148.1, mailed Mar. 28, 2025.

* cited by examiner

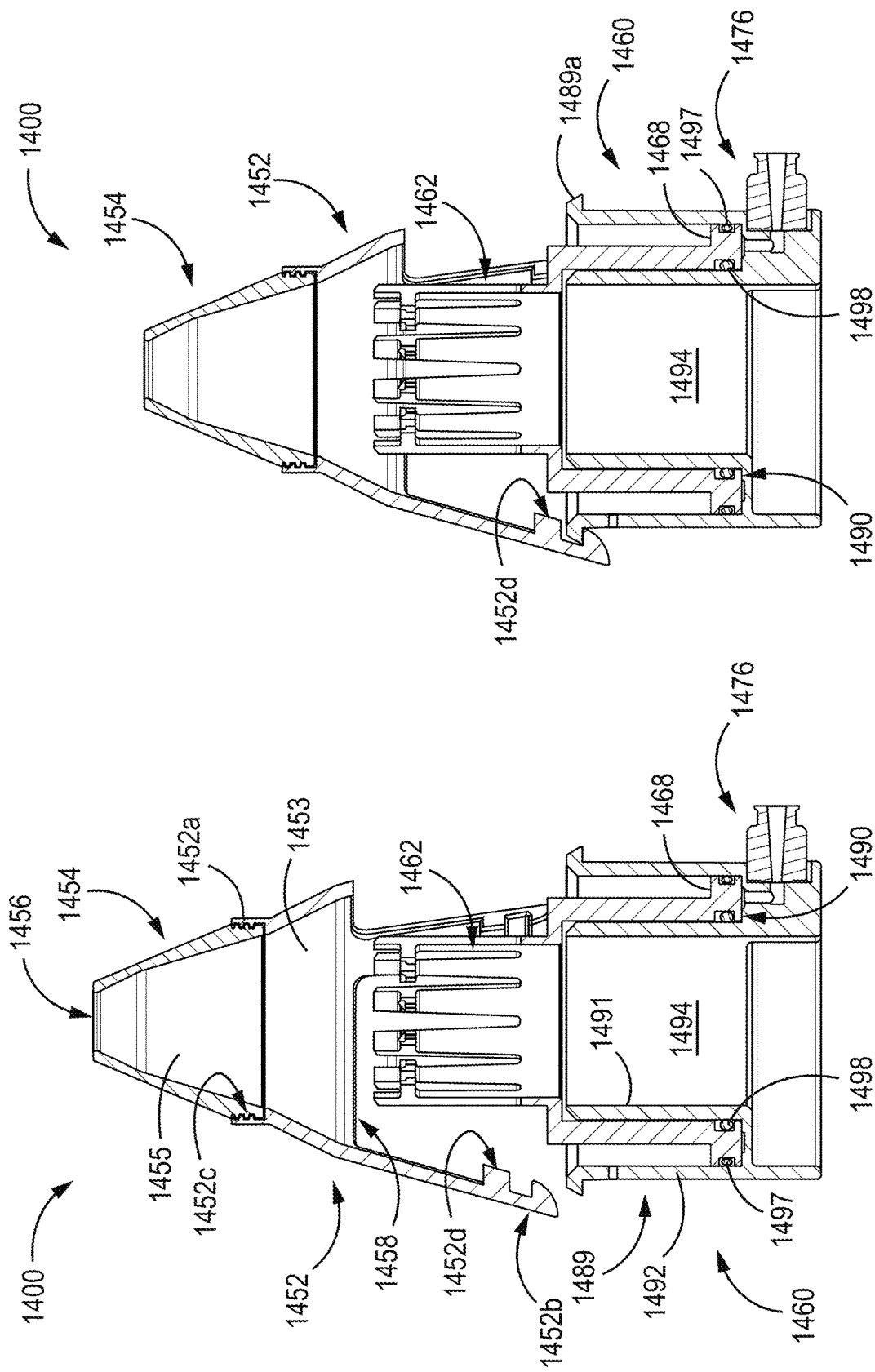

HYDRAULIC CRIMPING DEVICE

CROSS-REFERENCE TO RELATED APPLICATION

The present application is a division of U.S. patent application Ser. No. 17/124,021, filed Dec. 16, 2020, which claims the benefit of prior U.S. Provisional Appl. No. 62/951,918, filed Dec. 20, 2019, both which are incorporated by reference herein in their entirety.

TECHNICAL FIELD

The disclosure relates to systems and techniques for crimping medical devices, such as prosthetic heart valves.

BACKGROUND

Medical devices such as prosthetic heart valves may be delivered to a target site in a patient using percutaneous catheterization techniques. This may require the prosthetic heart valve device to assume a configuration featuring a relatively small cross-sectional dimension to allow for the percutaneous delivery via a catheter. Once delivered and placed in the target site, the prosthetic heart valve device may expand to assume a larger cross-sectional dimension. Accordingly, these prosthetic heart valve devices may be compacted or compressed before implantation in a patient, so that the prosthetic heart valve device may be loaded into the catheter and advanced to a treatment location in the body via a percutaneous catheterization technique.

SUMMARY

In some examples, this disclosure describes a crimping device for reducing the size of prosthetic heart valve devices and other medical devices. The crimping device is configured to reduce a dimension of a prosthetic heart valve device to allow for containment of the prosthetic heart valve device within a catheter or capsule. The crimping device utilizes a funnel to provide substantially uniform compression forces to the prosthetic heart valve device as a pusher translates the prosthetic heart valve device into the funnel. A central axis of the crimping device intersects a distal opening and a proximal opening of the funnel, and the piston is configured to translate toward the funnel in a direction substantially parallel to the central axis. The piston is configured to slidably translate within a piston cylinder. A system may comprise the crimping device and a prosthetic heart valve device positioned between the pusher and the funnel.

In some examples, the crimping device includes a funnel attached to a housing. The funnel includes a distal opening and a proximal opening and defines a central axis, with the central axis intersecting the distal opening and the proximal opening. The distal opening defines a distal opening dimension and the proximal opening defines a proximal opening dimension, with the distal opening dimension greater than the proximal opening dimension. A piston cylinder comprising a fluid port is attached to the housing, with the distal opening between the piston cylinder and the proximal opening. A piston is configured to slidably translate in the piston cylinder over a stroke length. A pusher is between the piston and the distal opening, and some portion of the is between the distal opening and the proximal opening when the piston slidably translates toward the funnel over the stroke length.

A technique includes placing a prosthetic heart valve device between a pusher comprising a crimping device and a distal opening of a funnel comprising the crimping device. The technique includes delivering a pressurized fluid to a piston cylinder of the medical crimping device, translating a piston within the piston cylinder in a direction toward a distal opening of the funnel and substantially parallel to a central axis, where the central axis intersects the distal opening of the funnel and a proximal opening of the funnel. The technique includes displacing the pusher in the direction substantially parallel to the central axis using the translation of the piston, and advancing the prosthetic heart valve device toward the distal opening of a funnel using the displacement of the pusher.

Clause 1: In some examples, a medical crimping device comprises: a housing; a funnel attached to the housing, wherein the funnel comprises a distal opening and a proximal opening, and wherein a central axis intersects the distal opening and the proximal opening, and wherein the funnel tapers down from the distal opening to the proximal opening; a piston cylinder attached to the housing; a piston within the piston cylinder, wherein the piston is configured to slidably translate in the piston cylinder in a direction substantially parallel to the central axis; and a pusher between the piston and the funnel, wherein the piston is configured to displace the pusher in the direction substantially parallel to the central axis when the piston slidably translates in the piston cylinder.

Clause 2: In some examples of the medical crimping device of clause 1, the piston has a stroke length and at least a portion of the pusher is between the distal opening and the proximal opening when the piston slidably translates toward the funnel over the stroke length.

Clause 3: In some examples of the medical crimping device of clause 1 or 2, the pusher comprises a pusher base and a plurality of fingers extending from the pusher base.

Clause 4: In some examples of the medical crimping device of clause 3, the plurality of fingers is configured to insert into the funnel through the distal opening when the piston displaces the pusher in the direction substantially parallel to the central axis.

Clause 5: In some examples of the medical crimping device of clause 3 or 4, each finger in the plurality of fingers extends from a pivoting end to a free end, wherein the pivoting end is attached to the pusher base and the pivoting end is configured to pivot when the central axis intersects the pusher base and a force toward the central axis is applied to the free end.

Clause 6: In some examples of the medical crimping device of any of clauses 3-5, the pusher defines a maximum dimension substantially perpendicular to the central axis when the central axis intersects the base, and wherein the distal opening of the funnel defines a distal opening dimension substantially perpendicular to the central axis, wherein the maximum dimension is less than the distal opening dimension.

Clause 7: In some examples of the medical crimping device of any of clauses 1-6, the piston cylinder comprises a fluid port, wherein the fluid port is fluid communication with the piston.

Clause 8: In some examples of the medical crimping device of any of clauses 1-7, the piston cylinder is an annular cylinder defining a central lumen, wherein the central lumen surrounds the central axis, and wherein the pusher comprises a pusher opening surrounding the central axis.

Clause 9: In some examples of the medical crimping device of any of clauses 1-8, either the pusher or the piston defines a protrusion, and the other of the pusher or the piston defines a recess configured to receive the protrusion.

Clause 10: In some examples of the medical crimping device of any of clauses 1-9, the distal opening of the funnel defines a distal opening dimension substantially perpendicular to the central axis and the proximal opening of the funnel defines a proximal opening dimension substantially perpendicular to the central axis, wherein the distal opening dimension is greater than the proximal opening dimension, and wherein the distal opening is between the proximal opening and the piston cylinder.

Clause 11: In some examples of the medical crimping device of clause 10, the funnel defines a first taper and a second taper between the distal opening and the proximal opening, wherein an angle of the first taper relative to the central axis is greater than an angle of the second taper relative to the central axis.

Clause 12: In some examples of the medical crimping device of clause 10 or 11, the funnel comprises a distal funnel section comprising the distal opening and a proximal funnel section comprising the proximal opening, wherein the proximal funnel section is mechanically attached to the distal funnel section.

Clause 13: In some examples of the medical crimping device of any of clauses 10-12, the funnel comprises a surface of revolution around central axis and facing the central axis, wherein a generatrix of the surface of revolution is concave down relative to the central axis.

Clause 14: In some examples, a system comprises the medical crimping device of any of clauses 1-13 and a prosthetic heart valve in mechanical communication with the pusher, wherein the pusher is configured to displace the prosthetic heart valve toward the funnel when the piston displaces the pusher in the direction along the central axis.

Clause 15: In some examples, a medical crimping device comprises a housing; a funnel attached to the housing, wherein the funnel defines a central axis, wherein the funnel comprises a distal opening and a proximal opening and the central axis intersects the distal opening and the proximal opening, and wherein the distal opening of the funnel defines a distal opening dimension substantially perpendicular to the central axis and the proximal opening of the funnel defines a proximal opening dimension substantially perpendicular to the central axis, wherein the distal opening dimension is greater than the proximal opening dimension; a pusher; a piston cylinder attached to the housing, the piston cylinder comprising a fluid port, wherein the distal opening is between the piston cylinder and the proximal opening; and a piston within the piston cylinder, wherein the pusher is between the piston and the funnel; wherein the piston is configured to slidably translate over a stroke length in the piston cylinder in a direction substantially parallel to the central axis, wherein the piston is configured to displace the pusher in the direction substantially parallel to the central axis when the piston slidably translates in the piston cylinder and some portion of the pusher is between the distal opening and the proximal opening when the piston slidably translates toward the funnel over the stroke length, and wherein the fluid port in fluid communication with the piston.

Clause 16: In some examples of the medical crimping device of clause 15, the pusher comprises a pusher base and a plurality of fingers extending from the pusher base, and wherein the plurality of fingers is configured to insert into the funnel through the distal opening when the piston displaces the pusher in the direction substantially parallel to the central axis.

Clause 17: In some examples of the medical crimping device of clause 16, each finger in the plurality of fingers extends from a pivoting end to a free end, wherein the pivoting end is attached to the pusher base and the pivoting end is configured to pivot when the central axis intersects the pusher base and a force toward the central axis is applied to the free end.

Clause 18: In some examples of the medical crimping device of clause 15, the piston cylinder is an annular cylinder surrounding a central lumen, wherein the central lumen surrounds the central axis, and wherein the pusher comprises a pusher opening surrounding the central axis.

Clause 19: In some examples, a method comprises: placing a prosthetic heart valve device between a pusher comprising a crimping device and a distal opening of a funnel comprising the crimping device; delivering a pressurized fluid to a piston cylinder of the medical crimping device; translating a piston within the piston cylinder in a direction substantially parallel to a central axis using the supplied pressurized fluid, wherein the central axis intersects the distal opening of the funnel and a proximal opening of the funnel, and wherein the distal opening is between the proximal opening and the piston cylinder; displacing the pusher in the direction substantially parallel to the central axis using the translation of the piston; and advancing the prosthetic heart valve device in the direction along the central axis and toward the distal opening of a funnel using the displacement of the pusher.

Clause 20: In some examples of the method of clause 19, the method comprises advancing the prosthetic heart valve device into the funnel; contacting the prosthetic heart valve device and an interior surface of the funnel; and compressing the prosthetic heart valve device using the contact between the prosthetic heart valve device and the interior surface of the funnel.

The details of one or more examples are set forth in the accompanying drawings and the description below. Other features, objects, and advantages will be apparent from the description and drawings, and from the claims.

BRIEF DESCRIPTION OF DRAWINGS

FIG. 15 is a cross-sectional illustration of the crimping device of FIG. 14 with a housing detached from a piston cylinder thereof.

FIG. 16 is a cross-sectional illustration of the crimping device of FIG. 14 with a housing attached to a piston cylinder thereof.

DETAILED DESCRIPTION

Figure 1:
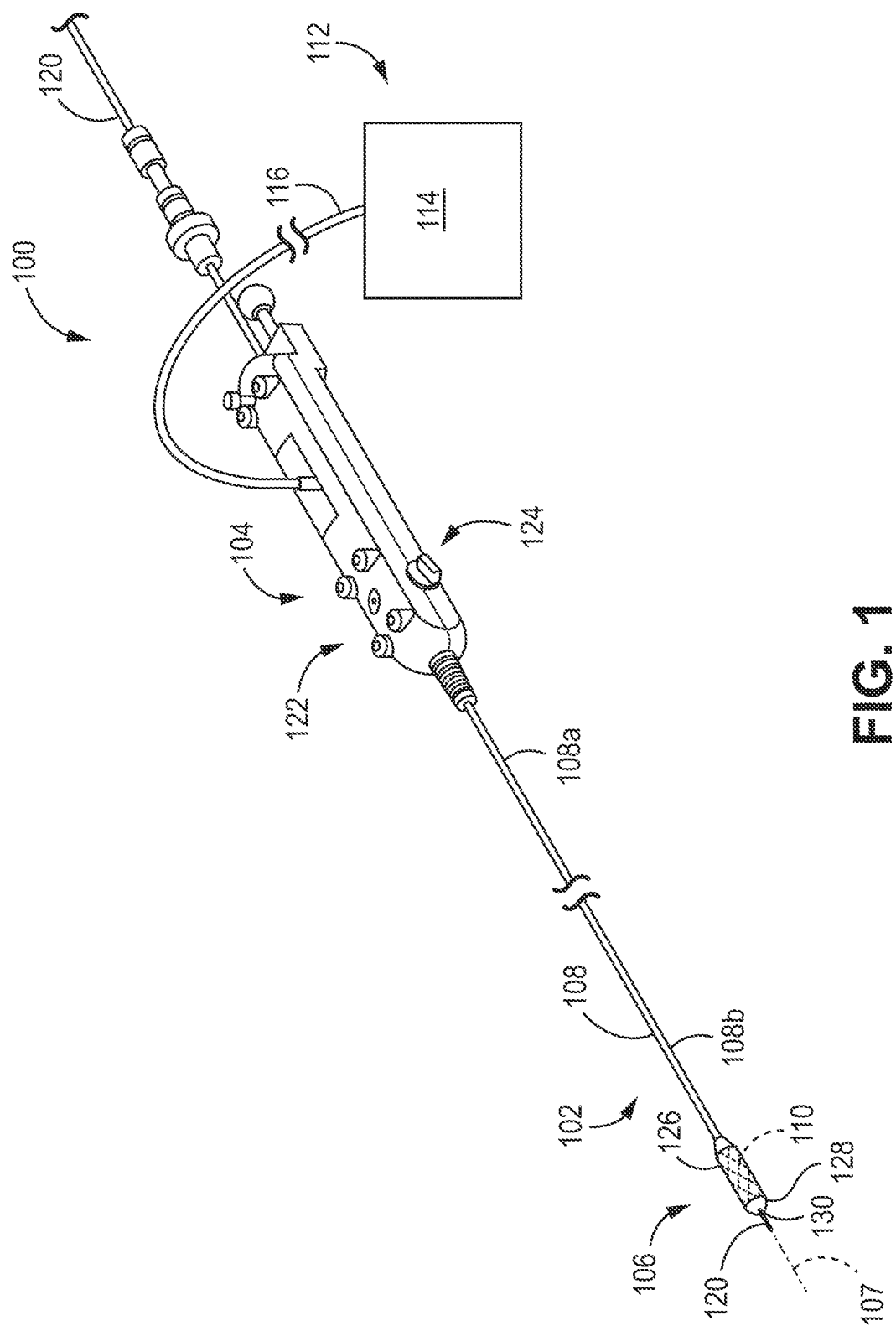
FIG. 1 is an isometric view of an example system for delivering an example prosthetic heart valve device.

Prosthetic heart valve devices may be introduced into a lumen of a body vessel via percutaneous catheterization techniques. These prosthetic heart valve devices may be configured with a delivery configuration featuring a relatively small cross-sectional dimension to allow for percutaneous delivery to a treatment site via a catheter. In some prosthetic heart valve devices, the relatively small cross-sectional dimension allows for containment within a delivery capsule. Once delivered to the target site and deployed by a clinician, the prosthetic heart valve device may be configured to expand from the delivery configuration and assume a larger cross-sectional dimension. In the expanded state, the prosthetic heart valve device may have a larger cross-sectional dimension than the catheter and/or the capsule used for delivery. Accordingly, a crimping device may be used to crimp (e.g., reduce) a cross-sectional dimension of the prosthetic heart valve device to allow loading into the catheter and advancement to a treatment location in the body via a percutaneous catheterization technique.

Prosthetic heart valve devices may have a relatively large expanded cross-sectional dimension (e.g., about 1.97 inches or more). In some cases, prosthetic heart valve devices may be packaged and stored in an expanded state until just before implantation into a patient. Consequently, during an implantation procedure, prosthetic heart valve devices are often crimped in the operating room from an expanded cross-sectional dimension to a delivery configuration suitable for delivery via a delivery capsule. Further, the prosthetic heart valve device may be stored in a sterile solution (e.g., a saline solution) until the prosthetic heart is loaded into the delivery capsule of a delivery system. This may necessitate the crimping process occur while the prosthetic heart valve device remains submerged in the sterile solution. Such procedures benefit from crimping devices that are highly portable and readily available to perform crimping with the prosthetic heart valve device in the submerged state. Further, such procedures may benefit from systems which minimize the use of direct hand strength to provide the crimping force. A required use of direct hand strength (e.g., twisting or pushing forces directly applied by hand) in order to generate crimping forces on a prosthetic heart valve device may result in varying levels of discomfort due to variations in strength among individual clinicians. The required use of direct hand strength for crimping may also require a clinician's hands to be submerged for some extended period of time, when the prosthetic heart valve device remains submerged in sterile solution during the crimping.

In some examples, the disclosure relates to a hydraulically driven crimping device. The crimping device disclosed is configured to utilize a pusher and a funnel to crimp a prosthetic heart valve device. The crimping device is configured to precipitate contact between the prosthetic heart valve device and an internal surface of the funnel by positioning the prosthetic heart valve device on the pusher and translating the pusher into the large opening of the funnel. The internal surface of the funnel exerts substantially uniform inward radial forces on the prosthetic heart valve device as the pusher drives the prosthetic heart valve device into the funnel. The pusher may be configured to flex or pivot toward a center axis defined by the funnel as the tapering internal surface of the funnel exerts inward radial forces on the prosthetic heart valve device.

The crimping device displaces the pusher in a direction substantially parallel to the central axis of the funnel using a hydraulic piston. A pressurized fluid delivered to the hydraulic piston causes the hydraulic piston to slidably translate in a piston cylinder, and causes the pusher to displace toward the funnel. In this manner, the pressurized fluid causes the translation of the pusher to precipitate contact between the prosthetic heart valve device and the internal surface of the funnel, in order to crimp the prosthetic heart valve device in preparation for loading into a delivery system.

The crimping device allows the crimping of prosthetic heart valve devices into a relatively smaller cross-sectional dimension in the operating room during an implantation procedure. The hydraulically actuated device and the tapering internal surface of the funnel allows the crimping to occur in a relatively controlled manner without the necessity for extensive manual manipulation of the device. Additionally, the hydraulic operation allows the crimping device to be actuated from a position external to a required environment surrounding the prosthetic heart valve device, such as a chilled saline solution.

In some examples, the present disclosure is directed to systems including crimping devices for reducing the size of prosthetic heart valve devices and other prosthetic heart valve devices. The term "crimp" (e.g., used in relation to a crimping device or a crimping method) may refer to devices and methods that compact or compress a prosthetic heart valve device to a smaller size. For example, the term "crimp" may refer to devices and methods that compact or compress a prosthetic heart valve device such as a prosthetic mitral valve device from an expanded cross-sectional dimension to a smaller cross-sectional dimension that allows for percutaneous delivery to a treatment site such as a mitral valve via a catheter and/or capsule. In examples, the term "crimp" may refer to the application of inward radial compression forces on a prosthetic heart valve device. The inward radial compression forces may reduce a cross-sectional dimension of the prosthetic heart valve device.

Generally, the mitral valve or other type of atrioventricular valve can be accessed through a patient's vasculature in a percutaneous manner for delivery of valve replacement devices. By percutaneous it is meant that a location of the vasculature remote from the heart is accessed through the skin, typically using a surgical cut down procedure or a minimally invasive procedure. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as described herein.

Expanding valve replacement devices may be delivered through a patient's vasculature in a percutaneous manner utilizing appropriately configured delivery systems. FIG. 1 is an isometric view of one such example system 100 for delivering a crimped device such as a prosthetic heart valve device. The system 100 may include a catheter 102 having an elongated catheter body 108, and may include a delivery capsule 106. The catheter body 108 may include a proximal portion 108a and a distal portion 108b carrying the delivery capsule 106. The delivery capsule 106 may contain a crimped medical device such as prosthetic heart valve device 110 (shown schematically in broken lines).

A control unit 104 coupled to the proximal portion 108a of catheter body 108 may provide steering capability (e.g., 360 degree rotation of the delivery capsule 106, 180 degree rotation of the delivery capsule 106, 3-axis steering, 2-axis steering, etc.) used to deliver the delivery capsule 106 to a target site (e.g., to a native mitral valve) and deploy the crimped prosthetic heart valve device at the target site. The catheter 102 can be configured to travel over a guidewire 120, which can be used to guide the delivery capsule 106 into, for example, a native heart valve. The system 100 may also include a fluid assembly 112 configured to supply fluid to and receive fluid from the catheter 102 to, for example, cause the delivery capsule 106 to deploy the prosthetic heart valve device 110. The fluid assembly 112 may include a fluid source 114 and a fluid line 116 fluidically coupling the fluid source 114 to the catheter 102. The fluid source 114 may contain a flowable substance (e.g., water, saline, etc.) in one or more reservoirs.

The control unit 104 can include a control assembly 122 and a steering mechanism 124. For example, the control assembly 122 can include rotational elements, such as a knob, that can be rotated to rotate the delivery capsule 106 about its longitudinal axis 107. The control assembly 122 can also include features that allow a clinician to control deployment mechanisms of the delivery capsule 106 and/or the fluid assembly 112. For example, the control assembly 122 can include buttons, levers, and/or other actuators that initiate unsheathing and/or resheathing the prosthetic heart valve device 110. The steering mechanism 124 can be used to steer the catheter 102 through the anatomy by bending the distal portion 108b of the catheter body 108 about a transverse axis. In other embodiments, the control unit 104 may include additional and/or different features that facilitate delivering the prosthetic heart valve device 110 to the target site.

The delivery capsule 106 may include a capsule housing 126 configured to carry the prosthetic heart valve device 110 in a containment configuration and, optionally, an end cap 128 that extends distally from the capsule housing 126 and encloses the prosthetic heart valve device 110 in the capsule housing 126. The end cap 128 may have an opening 130 at its distal end through which the guidewire 120 can be threaded to allow for guidewire delivery to the target site. As shown in FIG. 1, the end cap 128 can also have an atraumatic shape (e.g., a partially spherical shape, a frusto-conical shape, blunt configuration, rounded configuration, etc.) to facilitate atraumatic delivery of the delivery capsule 106 to the target site. In certain embodiments, the end cap 128 can also house a portion of the prosthetic heart valve device 110.

Figure 2A:
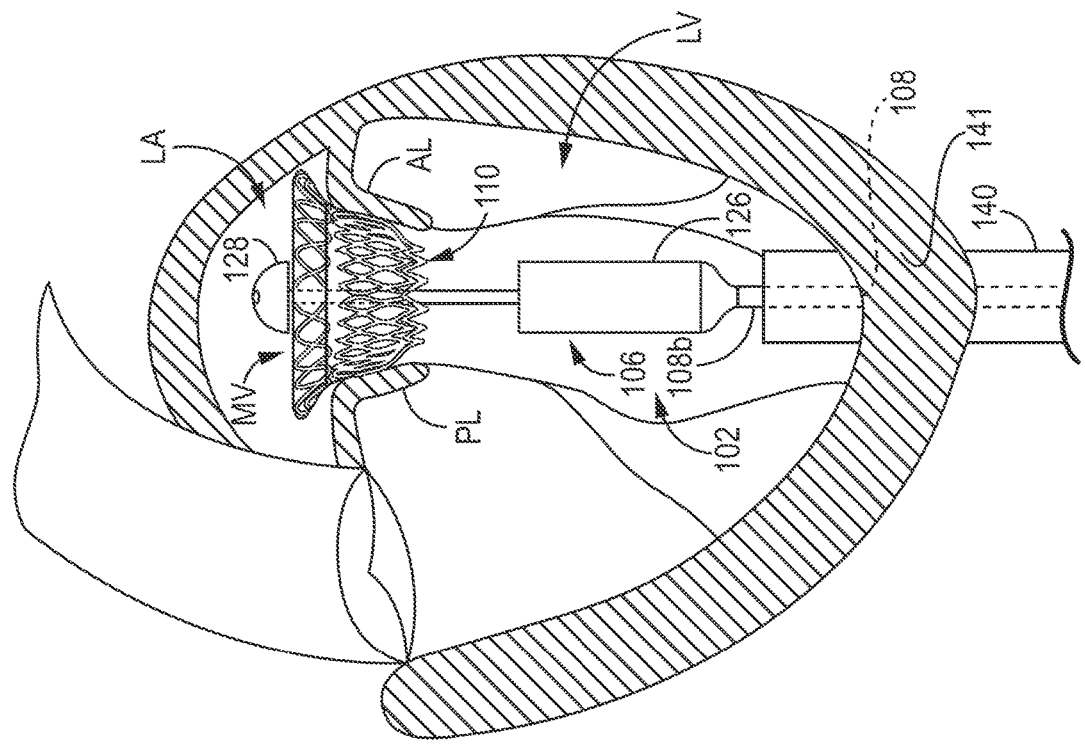
FIG. 2A is a schematic illustration of a distal portion of a delivery system positioned in a native mitral valve of a heart using a trans-apical delivery approach.
Figure 2B:
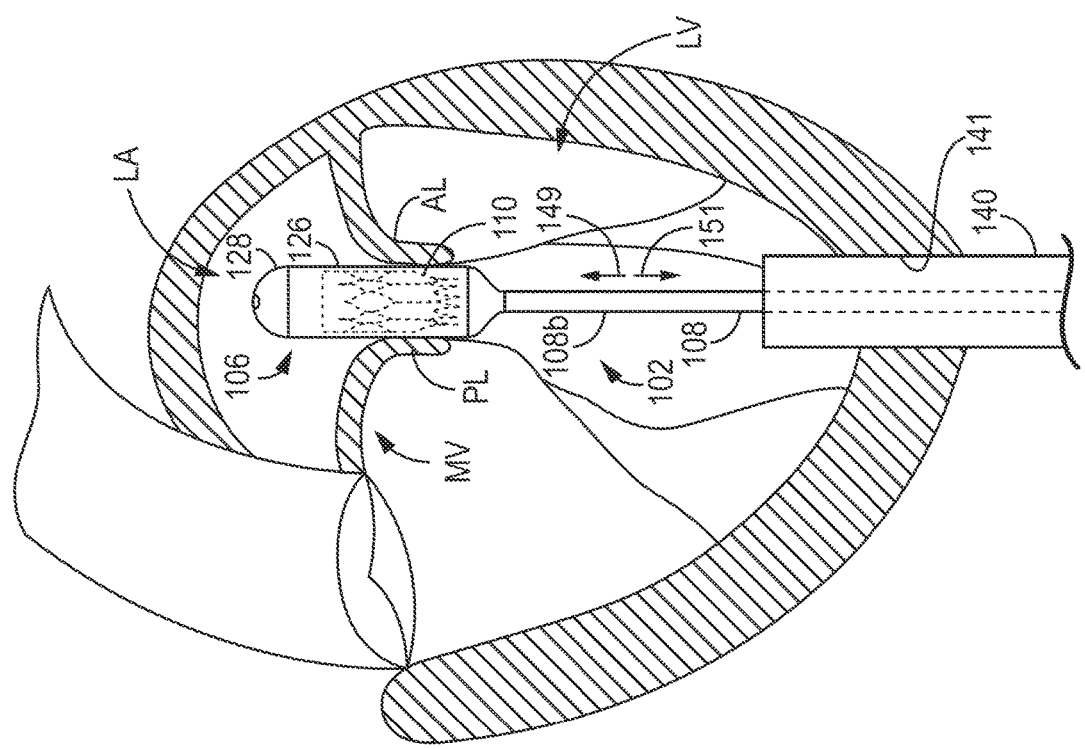
FIG. 2B is a schematic illustration of the distal portion of the system of FIG. 2A in a deployment configuration and a deployed example prosthetic heart valve device.

FIG. 2A and 2B illustrate the prosthetic heart valve device 110 in the containment configuration (FIG. 2A) and in the deployment configuration (FIG. 2B). For the purpose of illustration, FIG. 2A and FIG. 2B illustrate a portion of the system 100 positioning the prosthetic heart valve device 110 in a native mitral valve of a heart using a trans-apical delivery approach. Other approaches may be utilized, such as a trans-septal delivery approach. Referring to FIG. 2A, the guide catheter 140 is positioned in a trans-apical opening 141 to provide access to the left ventricle LV, with the catheter 102 extending through the guide catheter 140 such that the distal portion 108b of the catheter body 108 projects beyond the distal end of the guide catheter 140. The delivery capsule 106 may then be positioned between a posterior leaflet PL and an anterior leaflet AL of a mitral valve MV. Using the control unit 104 (FIG. 1), the catheter body 108 can be moved in the superior direction (as indicated by arrow 149), the inferior direction (as indicated by arrow 151), and/or rotated along the longitudinal axis of the catheter body 108 to position the delivery capsule 106 at a desired location and orientation within the opening of the mitral valve MV.

At the target location, the delivery capsule 106 can be driven from the containment configuration (FIG. 2A) towards the deployment configuration (FIG. 2B) to partially or fully deploy the prosthetic heart valve device 110 from the delivery capsule 106. Referring to FIG. 2B, in trans-apical delivery approaches, an example device such as prosthetic heart valve device 110 may be deployed from the delivery capsule 106 by drawing the capsule housing 126 proximally (i.e., further into the left ventricle LV) and, optionally, moving the end cap 128 distally (i.e., further into the left atrium LA). As the prosthetic heart valve device 110 exits the capsule housing 126, the prosthetic heart valve device 110 may expand to secure the prosthetic heart valve device 110 in the mitral valve MV.

The examples provided are described herein with reference to devices, systems, and methods for crimping, loading, and delivering prosthetic heart valve devices to a native mitral valve. However, other applications and other embodiments in addition to those described herein are within the scope of the present technology. For example, at least some embodiments of the present technology may be useful for delivering prosthetics to other native valves, such as the tricuspid valve or the aortic valve.

As discussed, prosthetic heart valve devices may be packaged and stored in their expanded state until just before implantation into a patient. For example, a prosthetic heart valve device such as prosthetic heart valve device 110 may be stored in a sterile solution up until the time the prosthetic heart valve device is ready to be loaded into a delivery system such as system 100 (FIG. 1) for implantation. As a result, during an implantation procedure, prosthetic heart devices are often crimped in the operating room from an expanded cross-sectional dimension to a configuration suitable to fit into a delivery capsule such as a delivery capsule 106. Such procedures benefit from crimping devices that are highly portable and readily available as a sterile system.

Figure 3:
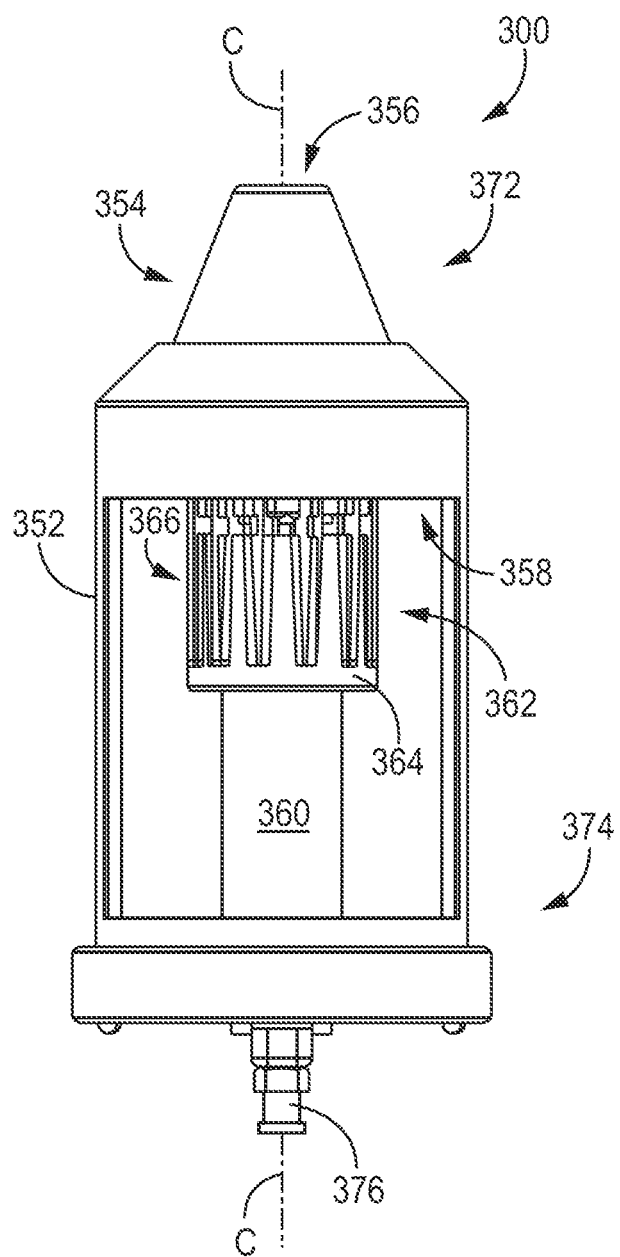
FIG. 3 is a schematic illustration of a crimping device.

FIG. 3 shows a schematic illustration of a crimping device 300 for reducing the size of a prosthetic heart valve device in accordance with the present technology. In particular, the crimping device 300 can be used to crimp or compact the prosthetic heart valve device to enable the prosthetic heart valve device to be loaded into a delivery system for percutaneously delivering the prosthetic heart valve device to a patient. In some embodiments, the prosthetic heart valve device can be a prosthetic heart valve device. For example, the prosthetic heart valve device may be a mitral valve device for implantation into a native mitral valve and the delivery system can be a delivery system for delivering the mitral valve device to the native mitral valve, such as one or more of the mitral valve devices and/or delivery systems disclosed in (1) International Patent Application NO. PCT/US2014/029549, filed Mar. 14, 2014, (2) International Patent Application NO. PCT/US2012/061219, filed Oct. 19, 2012, (3) International Patent Application NO. PCT/US2012/061215, filed Oct. 19, 2012, (4) International Patent Application NO. PCT/US2012/043636, filed Jun. 21, 2012, (5) U.S. patent application Ser. No. 15/490,047, filed Apr. 18, 2017, and (6) U.S. patent application Ser. No. 15/490,008, filed Apr. 18, 2017, each of which is incorporated herein by reference in its entirety.

As illustrated at FIG. 3, the crimping device 300 is configured to utilize a pusher 362 and a funnel 354 to crimp a prosthetic heart valve device placed between the pusher 362 and the funnel 354. With the prosthetic heart valve device appropriately positioned between the pusher 362 and the funnel 354, the crimping device 300 is configured to crimp the prosthetic heart valve device by translating the pusher 362 into the funnel 354 and precipitating contact between the prosthetic heart valve device and an internal surface of the funnel 354. The internal surface of the funnel 354 exerts substantially uniform inward radial forces on the prosthetic heart valve device as the pusher 362 drives the prosthetic heart valve device into the funnel 354. The internal surface of the funnel 354 tapers down from a larger distal opening 358 to a smaller proximal opening 356 in order to substantially maintain the inward radial forces around the prosthetic heart valve device as the prosthetic heart valve device decreases in size, and as the pusher 362 continues to translate the prosthetic heart valve device into the funnel 354. A portion of the pusher 362 may be configured to flex or pivot toward the center axis C as the internal surface of the funnel 354 exerts inward radial forces on the prosthetic heart valve device. For example, pusher 362 may include a base section 364 and a plurality of fingers 366, with one or more of the plurality of fingers 366 configured to pivot at base section 364 such that the one or more of the plurality of fingers 366 deflects inward toward central axis C in response to the inward radial forces exerted by funnel 354.

The crimping device 300 is configured to displace the pusher 362 in a direction substantially parallel to the central axis C using a piston-cylinder group 360 generally positioned at a distal end 374 of crimping device 300 ("crimping device distal end 374"). As will be discussed, a pressurized fluid delivered to the piston-cylinder group 360 via a fluid port 376 may cause a piston (not shown) within piston-cylinder group 360 to translate in a direction from the crimping device distal end 374 to a proximal end 372 of the crimping device 300 ("crimping device proximal end 372"). The piston may be mechanically coupled to the pusher 362, such that a hydraulically-driven displacement of the piston causes pusher 362 to translate in the direction substantially parallel to the central axis C. As discussed, translation of the pusher 362 in this manner may precipitate contact between a prosthetic heart valve device and the internal surface of the funnel 354, when the prosthetic heart valve device is positioned between the pusher 362 and the funnel 354. Funnel 354 and piston-cylinder group 360 are attached to a housing 352.

Regarding the terms "distal" and "proximal" within this description, unless otherwise specified, the terms may reference relative positions of a portion of a crimping device. In some examples, the terms may reference an operator of a crimping device and/or a location in the vasculature or heart. For example, "proximal" may refer to a position closer to the operator of a crimping device or an incision into the vasculature, and "distal" may refer to a position that is more distant from the operator of the crimping device or further from the incision along the vasculature; However, the terms "distal" and "proximal" are not limited to these descriptions. In some cases, an operator of a crimping device may be closer to a portion of the crimping device described as distal, may be more distant to a portion of the crimping device described as proximal.

Figure 4:
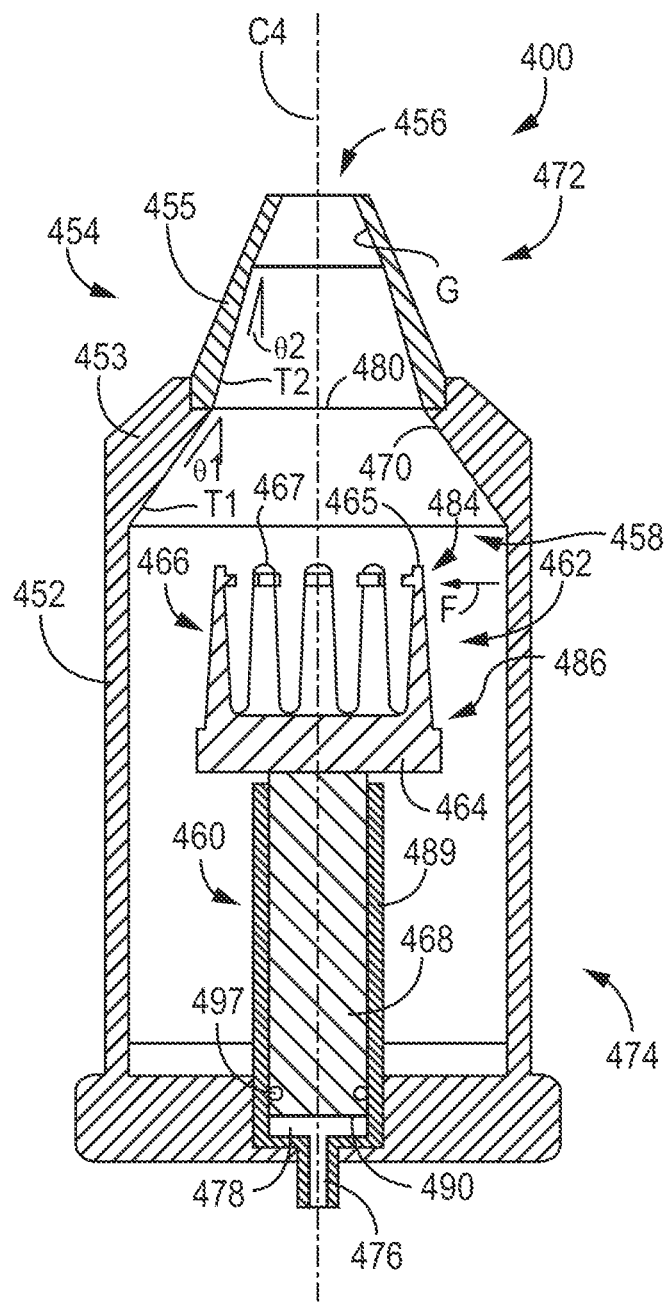
FIG. 4 is a cross-sectional illustration of the crimping device of FIG. 3.

A schematic illustration of a crimping device 400 is further illustrated at FIG. 4. FIG. 4 provides a schematic cross-section taken over a cutting plane perpendicular to a central axis C4. As illustrated, the central axis C4 intersects a distal opening 458 and a proximal opening 456 of funnel 454. Crimping device 400 includes a housing 452, a funnel 354, a proximal opening 356, a distal opening 358, a piston-cylinder group 360, a pusher 362, a crimping device proximal end 372, and a crimping device distal end 374, which may be configured similarly to and operate relative to other crimping device components in the same manner as the like-named components of the crimping device 300. Likewise, the components of the crimping device 400 discussed below may be present in the crimping device 300, and may be configured similarly to and operate relative to other crimping device components in the same manner as discussed for the crimping device 400.

An internal surface 470 of a funnel 454 at least partially surrounds the central axis C4 and extends between a distal opening 458 and a proximal opening 456 of the funnel 454. The internal surface 470 tapers down from the distal opening 458 to the proximal opening 456. A piston-cylinder group 460 comprises a piston cylinder 489 and a piston 468, with the piston 468 configured to slidably translate in the piston cylinder 489. A piston chamber 478 is bounded at least in part by the piston cylinder 489 and a portion of the piston 468. A pusher 462 is mechanically coupled with the piston 468, such that the piston 468 displaces the pusher 462 in a direction substantially parallel to the central axis C4 when the piston 468 slidably translates in the piston cylinder 489.

Here and elsewhere, when a displacement and/or length is substantially parallel to a central axis, this may mean a line parallel to the displacement and/or length is either parallel to the central axis or has an angle of intersection with the central axis of less than 30 degrees. In some examples, the angle of intersection may be less than 10 degrees, In some examples, the angle of intersection may be less than 5 degrees, and in other examples, less than 1 degree.

The pusher 462 may be configured to flex or pivot in order to accommodate the decreasing cross-sectional area of the internal surface 470 as the pusher 462 translates into the funnel 454 during a crimping operation. For example, the pusher 462 may comprise a base section 464 and a plurality of fingers 466 extending from the base section 464 toward the distal opening 458. Fingers such as a finger 465 and a finger 467 in the plurality of fingers 466 may be configured to pivot inward at the base section 464 in response to a force toward the central axis C4. The pivoting action may allow the pusher 462 to drive a prosthetic heart valve device positioned between the pusher 462 and the proximal opening 456 of the funnel 454 into contact with internal surface 470, so that the internal surface 470 may exert substantially uniform inward radial forces on the prosthetic heart valve device during a crimping operation.

Figure 5:
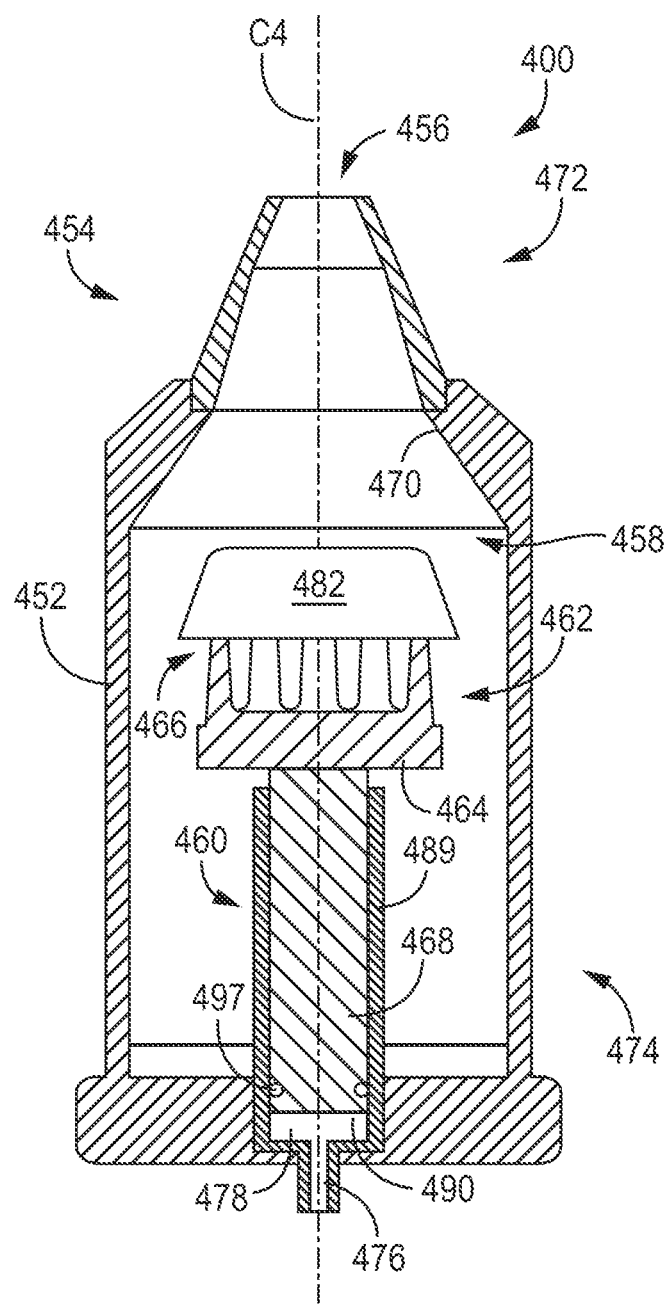
FIG. 5 is a cross-sectional illustration of the crimping device of FIG. 3 in an example configuration.

For example, FIG. 5 illustrates the crimping device 400 with a prosthetic heart valve device 482 positioned between the pusher 462 and the funnel 454. Prosthetic heart valve device 482 may be an example of prosthetic heart valve device 110 (FIG. 1, 2A, 2B). The piston 468 is configured to displace the pusher 462 in a direction substantially parallel to the central axis C4 when the piston 468 slidably translates in the piston cylinder 489. For example, a pressurized fluid may be delivered to piston chamber 478 via a fluid port 476, and the pressurized fluid may act on a piston head 490 to cause the piston 468 to slidably translate in the piston cylinder 489 in a direction from the crimping device distal end 474 to the crimping device proximal end 472. The sliding translation of the piston 468 may drive the pusher 462 and the prosthetic heart valve device 482 in a direction substantially parallel to the central axis C4 and toward the distal opening 458 of the funnel 454. An O-ring 497 may extend around the piston 468 to provide a fluid barrier between the piston chamber 478 and any clearances between the piston 468 and the piston cylinder 489.

Figure 6:
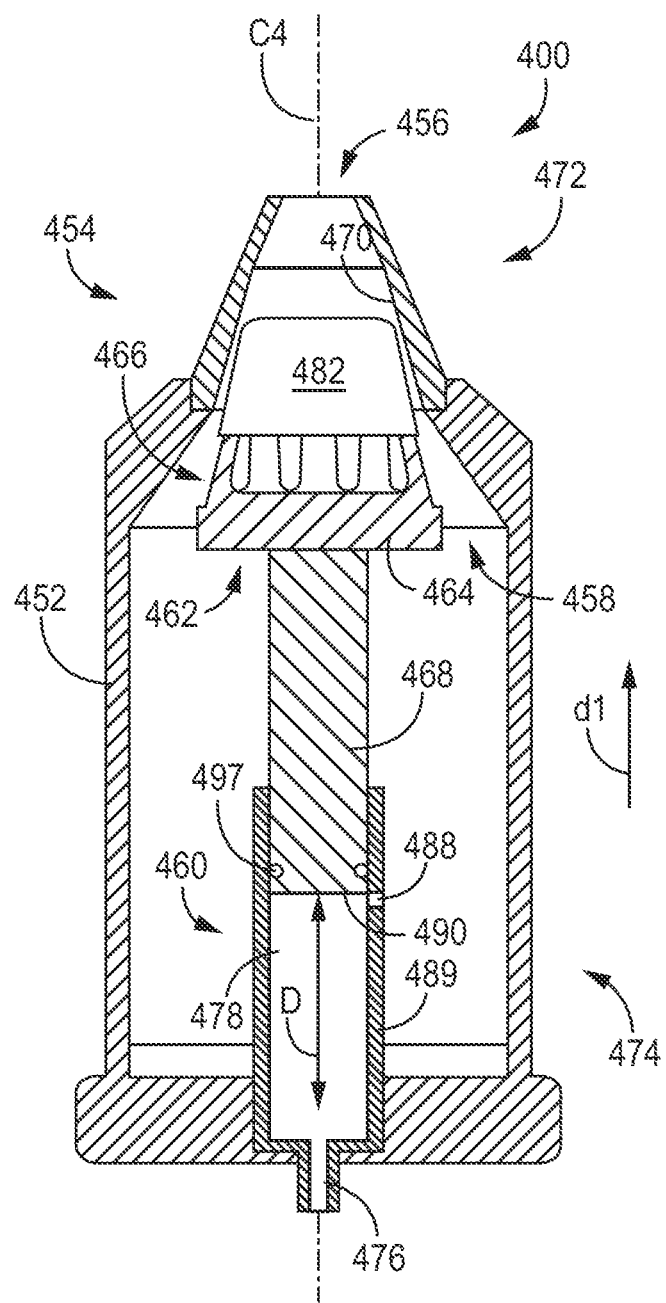
FIG. 6 is a cross-sectional illustration of the crimping device of FIG. 3 in another configuration.

FIG. 6 illustrates the crimping device 400 with the piston 468 having slidably translated over a stroke length D within the piston cylinder 489 as a result of, for example, a pressurized fluid supplied to the piston chamber 478 via the fluid port 476. The pusher 462, and the prosthetic heart valve device 482, have been displaced by the sliding translation of the piston 468 such that some portion of the pusher 462 is between the distal opening 458 and the proximal opening 456, and the prosthetic heart valve device 482 is in contact with the tapering internal surface 470 of funnel 454. The tapering internal surface 470 exerts substantially uniform inward radial forces (e.g., toward central axis C4) on the prosthetic heart valve device 482 as the pusher 462 drives the prosthetic heart valve device 482 from the distal opening 458 toward the proximal opening 456. Further, as the plurality of fingers 466 experience an inward radial force toward central axis C4 as prosthetic heart valve device 482 contacts internal surface 470, the plurality of fingers 466 pivot inward from base section 464 toward the central axis C, in order to accommodate the decreasing cross-sectional area of internal surface 470 as pusher 462 translates into funnel 454 during the crimping operation.

In this manner, the crimping device 400 is configured to utilize the pusher 462 and the funnel 454 to crimp the prosthetic heart valve device 482 when the prosthetic heart valve device 482 is appropriately positioned between the pusher 462 and the proximal opening 456 of the funnel 454. The crimping device 400 is configured to translate the pusher 462 into the funnel 454 and precipitate contact between prosthetic heart valve device 482 and the internal surface 470 of the funnel 454. The internal surface 470 exerts substantially uniform inward radial forces on prosthetic heart valve device 482 as the pusher 462 drives the prosthetic heart valve device 482 toward proximal opening 456. The internal surface 470 tapers down from the larger distal opening 458 to the smaller proximal opening 456 in order to substantially maintain the inward radial forces around the prosthetic heart valve device 482 as the prosthetic heart valve device 482 decreases in size and the pusher 462 continues to translate the prosthetic heart valve device 482 into funnel 454. Crimping device 400 may thus be utilized to crimp a prosthetic heart valve device such as prosthetic heart valve device 110 (FIG. 1, 2A, 2B) from an expanded cross-sectional dimension to a configuration suitable to fit into a delivery capsule such as a delivery capsule 106 (FIG. 1, 2A, 2B).

Returning to FIG. 4, the distal opening 458 and/or the proximal opening 456 of funnel 454 may be a rounded opening, such as a substantially circular opening, an elliptical opening, an oval shaped opening, and the like. The shape of distal opening 458 and/or proximal opening 456 may correspond to or otherwise be based on a shape of the prosthetic heart valve device to be compressed. As discussed, the distal opening 458 is generally a larger opening than the proximal opening 456. In examples, the distal opening 458 defines a distal opening dimension (e.g., a first diameter) substantially perpendicular to the central axis C, and the proximal opening 456 defines a proximal opening dimension (e.g., a second diameter) substantially perpendicular to the central axis C4, and the distal opening dimension is greater than the proximal opening dimension. In some examples, the pusher 462 defines a pusher dimension (e.g., a maximum diameter) substantially perpendicular to the central axis C4, and the distal opening dimension is greater than the pusher dimension. The distal opening 458 and/or the proximal opening 456 may be co-planer with a plane having any orientation relative to the central axis C4. The distal opening 458 and/or the proximal opening 456 may be co-planer with a plane intersected by the central axis C. In some examples, the distal opening 458 and/or the proximal opening 456 are co-planer with a plane substantially perpendicular to the central axis C4.

The internal surface 470 at least partially surrounds the central axis C4 and extends between the distal opening 458 and the proximal opening 456. The internal surface 470 may be configured to exert substantially uniform inward radial forces (e.g., toward the central axis C4) on a prosthetic heart valve device positioned between the pusher 462 and the funnel 454 as the pusher 462 drives the prosthetic heart valve device into the funnel 454. The internal surface 470 tapers down from the distal opening 458 to the proximal opening 456, and the taper may alter between the distal opening 458 and the proximal opening 456. The altering taper may be configured to accommodate a decreasing dimension (e.g., diameter) of the prosthetic heart valve device 482 as the prosthetic heart valve device is displaced toward proximal opening 456. The altering taper may be configured to substantially maintain a certain amount of inward radial force for a given prosthetic heart valve device 482 dimension (e.g., diameter) based on, for example, the expected size of a section of the prosthetic heart valve device 482 at a certain displacement between distal opening 458 and proximal opening 456.

In some examples, the internal surface 470 defines a first taper T1 and a second taper T2 between the distal opening 458 and the proximal opening 456, with the first taper T1 defining a first angle θ1 relative to the central axis C4 and the second taper T2 defining a second angle θ2 relative to the central axis C4. In examples, the first angle θ1 is greater than the second angle θ2. Here, an angle of a specific taper relative to the central axis C4 means the angle between a vector co-planer with the central axis C4 and parallel to a surface having the specific taper.

In some examples, some portion of the internal surface 470 may comprise a generatrix G, and the portion of the internal surface 470 may be a surface of revolution defined by a complete or partial revolution of the generatrix G around the central axis C4. The generatrix G may have an increasing or decreasing concavity in a direction from the crimping device distal end 474 toward the crimping device proximal end 472. In some examples, the first taper T1 is at least partially defined by a complete or partial revolution of a first generatrix around the central axis C4, and/or the second taper T2 is at least partially defined by a complete or partial revolution of a second generatrix around the central axis C4, where the first generatrix and/or the second generatrix may be a straight or curvilinear line segment.

The funnel 454 may comprise a distal funnel section 453 and a proximal funnel section 455. The internal surface 470 may comprise some portion of distal funnel section 453 and come portion of proximal funnel section 455. The distal funnel section 453 may comprise the distal opening 458, and the proximal funnel section 455 may comprise the proximal opening 456. The distal funnel section 453 and the proximal funnel section 455 may comprise discrete parts which meet at a section border 480 using a suitable connection mechanism. For example, the distal funnel section 453 and the proximal funnel section 455 may be configured to join and meet at the section border 480 with a threaded connection, an interference fit connection, a snap-fit connection, a spring-loaded connection, or any other type of connection suitable for joining the distal funnel section 453 and the proximal funnel section 455.

The plurality of fingers 466 may be configured to accommodate the taper of internal surface 470 as the plurality of fingers displace from the distal opening 458 toward the proximal opening 456. For example, one of more fingers of the plurality of fingers 466 such as the finger 465 may comprise a free end 484 and a pivoting end 486, with the pivoting end 486 attached to the base section 464 of pusher 462. The finger 465 may be configured to pivot toward the central axis C4 when the central axis C4 intersects the base section 464 and a force toward the central axis C4 such as F is applied to the free end 484. The finger 465 may be resiliently biased to return to a relaxed, substantially stress-free position when the force F is removed. Thus, the plurality of fingers 466 may be configured such that one or more fingers pivot inward as the plurality of fingers 466 displaces from the distal opening 458 toward the proximal opening 456, and internal surface 470 exerts forces toward central axis C4 on the one or more fingers. The one or more fingers such as finger 465 may return to a relaxed, substantially zero-stress position (such as illustrated at FIG. 3) when the plurality of fingers 466 is positioned between the distal opening 458 and the piston 468.

The pivoting end 486 may have any configuration suitable for finger 465 to pivot inward toward central axis C4. The pivoting end 486 allow be integrally formed with base section 464 and comprise a flexible material, with the flexible material having material properties that allow for elastic bending of the pivoting end 486 as internal surface 470 applies a force on finger 465 toward central axis C4. The pivoting end 486 may be a mechanical joint (e.g., a rotary joint) configured to pivot toward central axis C4 when internal surface 470 applies a force on finger 465 toward central axis C4.

The piston 468 may displace over a stroke length D (FIG. 6). The stroke length D may be substantially parallel to central axis C4. In examples, crimping device 400 is configured such that, when piston 468 displaces over a stroke length D in a direction d1 from the crimping device distal end 474 toward the crimping device proximal end 472, at least some portion of pusher 462 is proximal to distal opening 458. In some examples, when piston 468 displaces over a stroke length D in the direction d1, the distal opening 458 is between at least some portion of pusher 462 and the piston 468. In some examples, when piston 468 displaces over a stroke length D in the direction d1, at least some portion of pusher 462 is between the distal opening 458 and the proximal opening 456. Piston 468 may displace over a stroke length D in the direction d1 sufficient to position some portion of pusher 462 proximally beyond proximal opening 456, such that proximal opening 456 is between the portion of pusher 462 and piston 468.

In some examples, crimping device 400 is configured to establish a maximum stroke length of the piston 468, in order to reduce a risk of over-crimping, reduce burden on a clinician responsible for the delivery of pressurized fluid through fluid port 476, or for some other reason. For example, a cylinder vent 488 may be configured to establish fluid communication through piston cylinder 489. The cylinder vent 488 may be configured to extend through piston cylinder 489 such that, at the maximum stroke length of piston 468, piston head 490 has traveled proximally beyond cylinder vent 488 sufficiently to allow cylinder vent 488 to establish fluid communication between piston chamber 478 and an atmosphere and/or volume outside of piston chamber 478. The fluid communication via cylinder vent 488 may allow a pressurized fluid within piston chamber 478 to vent through cylinder vent 488 rather than fully acting on piston head 490, ceasing or reducing the displacement of piston 468 in the direction d1. In some examples, crimping device 400 may include a mechanical stop (not shown) which resists further displacement of piston 468 within piston cylinder 489 in the direction d1. The mechanical stop may be configured to contact or abut the piston 468 and prevent further travel in the direction d1 when the maximum stroke length is achieved. The mechanical stop may be affixed to piston cylinder 489, or affixed to some other portion of crimping device 400 such as housing 452, funnel 454, or some other section configured to remain stationary relative to the displacement of piston 468.

The piston 468 may mechanically engage the pusher 462 in any manner sufficient to cause displacement of the pusher 462 in a distal and/or proximal direction when the piston 468 translates within the piston cylinder 489. The pusher 462 may be attached to piston 468 using any suitable technique, such as, but not limited to, adhesives, engineering fits, fusion, friction, or welding or soldering. The connection between the pusher 462 and the piston 468 may be substantially permanent, or, alternatively, may be configured to enable separation of the pusher 462 and the piston 468, such that the pusher 462 and the piston 468 remain substantially usable upon separation. In some examples, pusher 462 and piston 468 mechanically communicate via a removable attachment which may be initiated and terminated manually by hand and without the use of additional tools. This may enable a clinician to relatively easily attach and detach pusher 462 from piston 468. This may be advantageous, for example, when a prosthetic heart valve device 110, 482 (FIG. 1, 2A, 2B, 5, 6) is configured to be loaded into a crimping device 400 with pusher 462 already in mechanical communication with prosthetic heart valve device 110, 482. For example, when prosthetic heart valve device 110, 482 is supplied attached to a pusher such as pusher 462.

Figure 7:
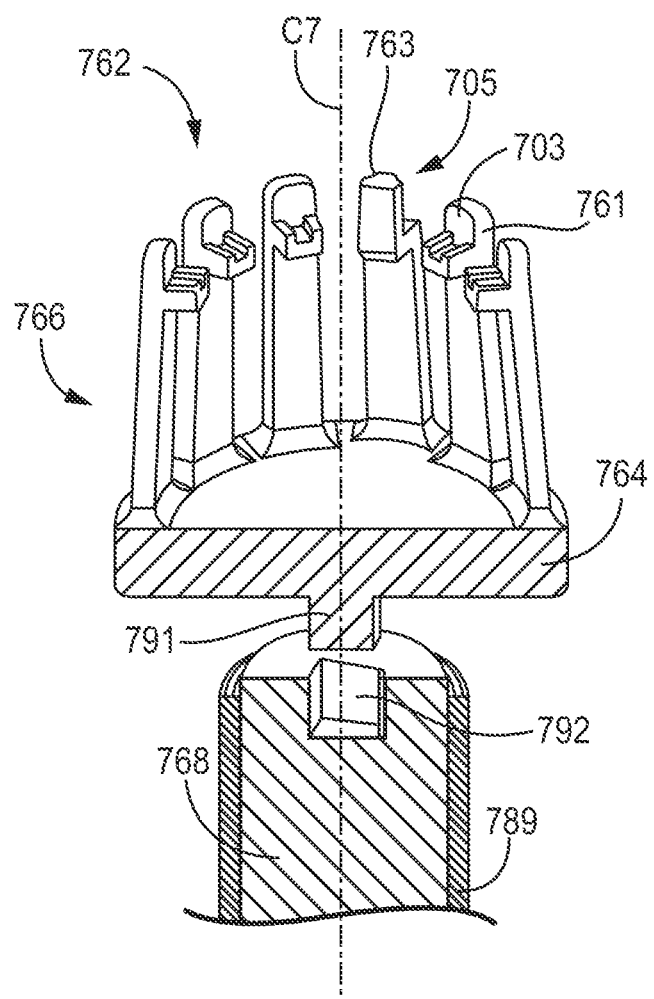
FIG. 7 is a cross-sectional illustration of a portion of an example crimping device.

In some examples, either the pusher 462 or the piston 468 may define a protrusion, and the other of the pusher 462 or the piston 468 may define a recess configured to receive the protrusion. FIG. 7 illustrates a portion of a crimping device 700 including a piston 768 configured to translate with a piston cylinder 789, and a pusher 762 including a base section 764 and plurality of fingers 766. FIG. 7 is a cross-section view taken over a cutting plane perpendicular to a central axis C7 extending through the portion of crimping device 700. Piston 768, piston cylinder 789, pusher 762, base section 764, and plurality of fingers 766 may be configured similarly to and operate relative to other crimping device components in the same manner as the like-named components of crimping device 300 and crimping device 400. As illustrated by FIG. 7, pusher 762 includes a protrusion 791 and piston 768 includes a recess 792. Recess 792 is configured to receive protrusion 791 to allow for mechanical engagement of pusher 762 with piston 768. This arrangement may enable relatively easily attachment and/or detachment of pusher 762 from piston 768 by a clinician during an implantation procedure or otherwise.

In some examples, the plurality of fingers may be configured to substantially maintain a prosthetic heart valve device between some portion of a first finger and some portion of a second finger comprising the plurality of fingers. The first finger and the second finger may be configured to have opposing bearing surfaces, where the bearing surfaces may be configured to engage opposite sides of a portion of a prosthetic heart valve device when the prosthetic heart valve device is positioned on the plurality of fingers. For example, FIG. 7 illustrates a first finger 761 having a bearing surface 703 ("first finger bearing surface 703") and a second finger 763 having a bearing surface 705 ("second finger bearing surface 705"). First finger bearing surface 703 may substantially face toward longitudinal axis C7 while second finger bearing surface 705 may substantially face away from longitudinal axis C7. In examples, when first finger 761 and second finger 763 are in a relaxed, substantially zero-stress position, first finger bearing surface 703 is displaced farther from central axis C7 than second finger bearing surface 705. In some examples, when a funnel such as funnel 354, 454 exerts a force on the plurality of fingers 766 in a direction toward central axis C7, first finger bearing surface 703 is displaced farther from central axis C7 than second finger bearing surface 705. First finger bearing surface 703 may be adjacent to a free end of first finger 761, and second finger bearing surface 705 may be adjacent to a free end of second finger 763.

Figure 8:
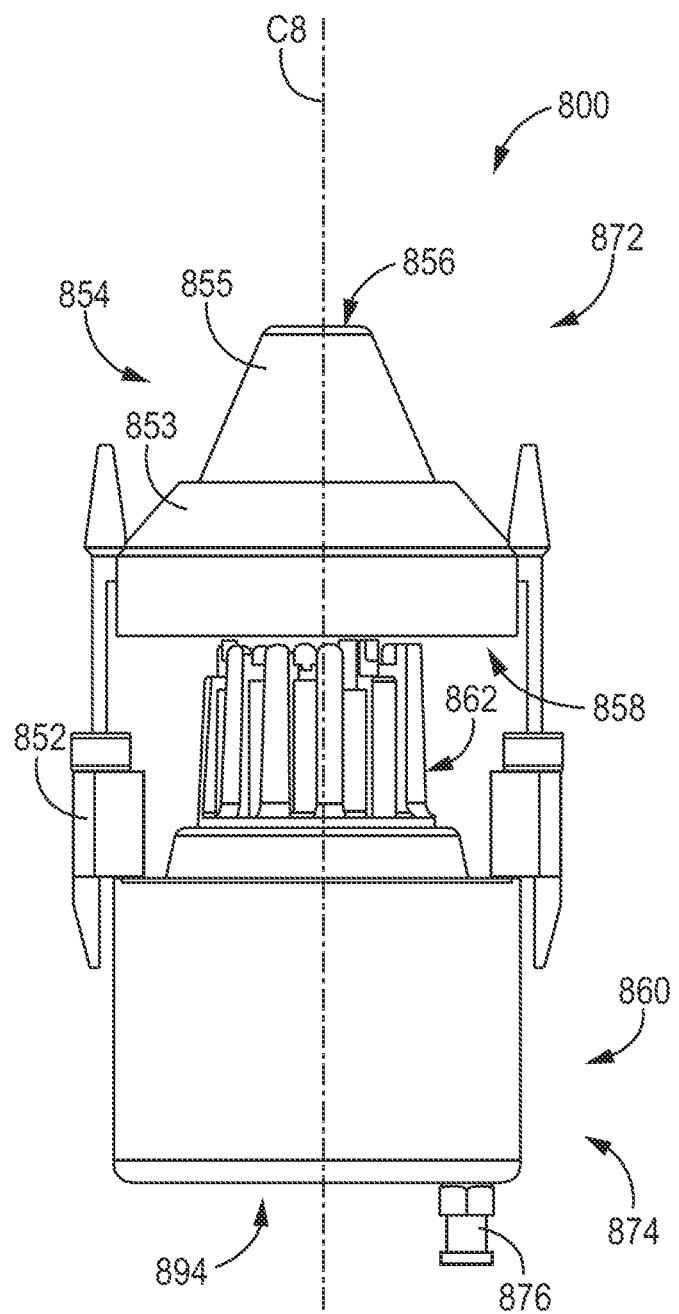
FIG. 8 is a schematic illustration of another example crimping device.
Figure 9:
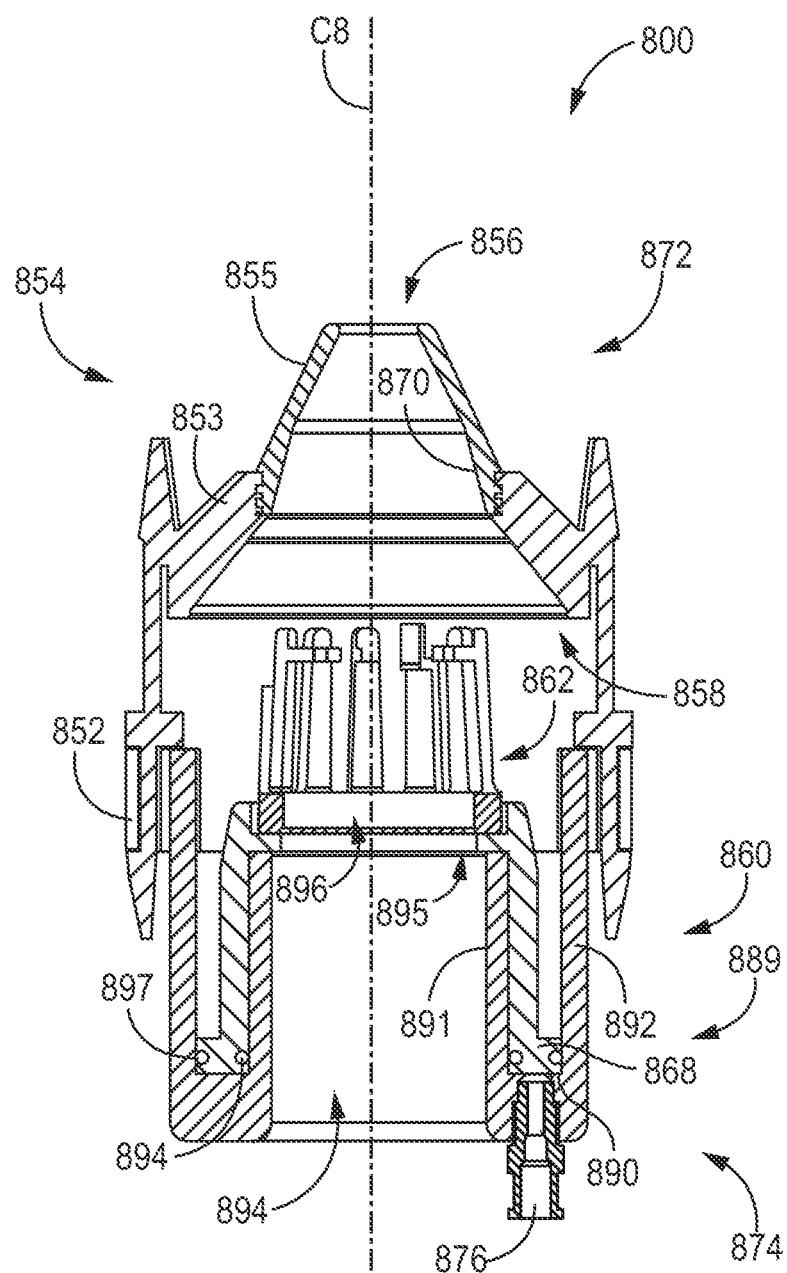
FIG. 9 is a cross-sectional illustration of the crimping device of FIG. 8.

The crimping device may include a central lumen extending centrally through the piston and the pusher. The central lumen may provide access by a delivery system such as delivery system 100 either distally or proximally. For example, FIG. 8 schematically illustrate a crimping device 800 including a central lumen 894. FIG. 9 provides a schematic cross-section of the crimping device 800 taken over a cutting plane perpendicular to a central axis C8, and illustrates the central lumen 894 extending into crimping device 800. Crimping device 800 includes a housing 852, a funnel 854, a distal funnel section 853, a proximal funnel section 855, a proximal opening 856, a distal opening 858, a piston-cylinder group 860 including a piston 868 (and piston head 890) and piston cylinder 889, a pusher 862, a crimping device proximal end 872, a crimping device distal end 874, a fluid port 876, and an O-ring 897, which may be configured similarly to and operate relative to other crimping device components in the same manner as the like-named components of the crimping device 300 and/or crimping device 400. Likewise, the components of the crimping device 800 discussed below may be present in the crimping device 300 and/or crimping device 400, and may be configured similarly to and operate relative to other crimping device components in the same manner as discussed for the crimping device 800.

As illustrated by FIG. 9, the central lumen 894 may extend through piston-cylinder group 860 and at least partially surround the central axis C8. The central axis C8 intersects the distal opening 858 and the proximal opening 856 of funnel 854. The central lumen 894 may be in fluid communication with a piston opening 895 and a pusher opening 896, such that the central lumen 894, the piston opening 895, and the pusher opening 896 substantially form a single passage accessible from both the crimping device proximal end 872 and the crimping device distal end 874. In some configurations, such as the transfemoral delivery system, it may be advantageous to pass the delivery system through the central lumen in order to attach a prosthetic heart valve device to a delivery system in an opposite orientation to other configurations, such as the transapical delivery system. This may allow for different directions of approach to the native anatomy and different deployment orientations for the clinician during use.

The central lumen 894 surrounds longitudinal axis C8 and extends through the piston cylinder 889. The piston cylinder 889 is configured to substantially surround some portion of the central lumen 894. The piston cylinder 889 may comprise an exterior wall 892 and an interior wall 891, where the interior wall 891 is between the exterior wall 892 and the central axis C8. The interior wall 891 may define an inner wall of the central lumen 894. The interior wall 891 and/or the exterior wall 892 may define any cross-section perpendicular to the central axis C8. For example, the interior wall 891 and/or the exterior wall 892 may define an elliptical (including circular) cross-section, an oval-shaped cross-section, a regular or irregular polygonal cross-section, or some other cross-sectional shape which surrounds at least some portion of the central axis C8.

The piston 868 is configured to translate within piston cylinder 889 and form a piston chamber bounded at least in part by piston cylinder 889 and a piston head 890 of piston 868. The O-ring 897 extends around an exterior-facing perimeter of piston 868 to provide a fluid barrier between the piston chamber formed and any clearances between piston 868 and exterior wall 892. A second O-ring 898 extends around an interior-facing perimeter of piston 868 to provide a fluid barrier between the piston chamber formed and any clearances between piston 868 and interior wall 891. A pressurized fluid delivered via a fluid port 876 may act on the piston head 890 and cause the piston 868 to translate in a direction from the crimping device distal end 874 to the crimping device proximal end 872. Fluid port 876 may comprise a Luer fitting or other type of suitable fitting for the delivery of a pressurized fluid.

The piston 868 is mechanically coupled to the pusher 862, such that a hydraulically-driven displacement of the piston 868 causes pusher 862 to translate in the direction substantially parallel to the central axis C8. In order to allow access throughout crimping device 800 (either proximally or distally), the pusher 862 may include pusher opening 896. Pusher opening 896 extends through pusher 862 and at least partially surrounds central axis C8. Pusher opening 896 is in fluid communication with central lumen 894.

Figure 10:
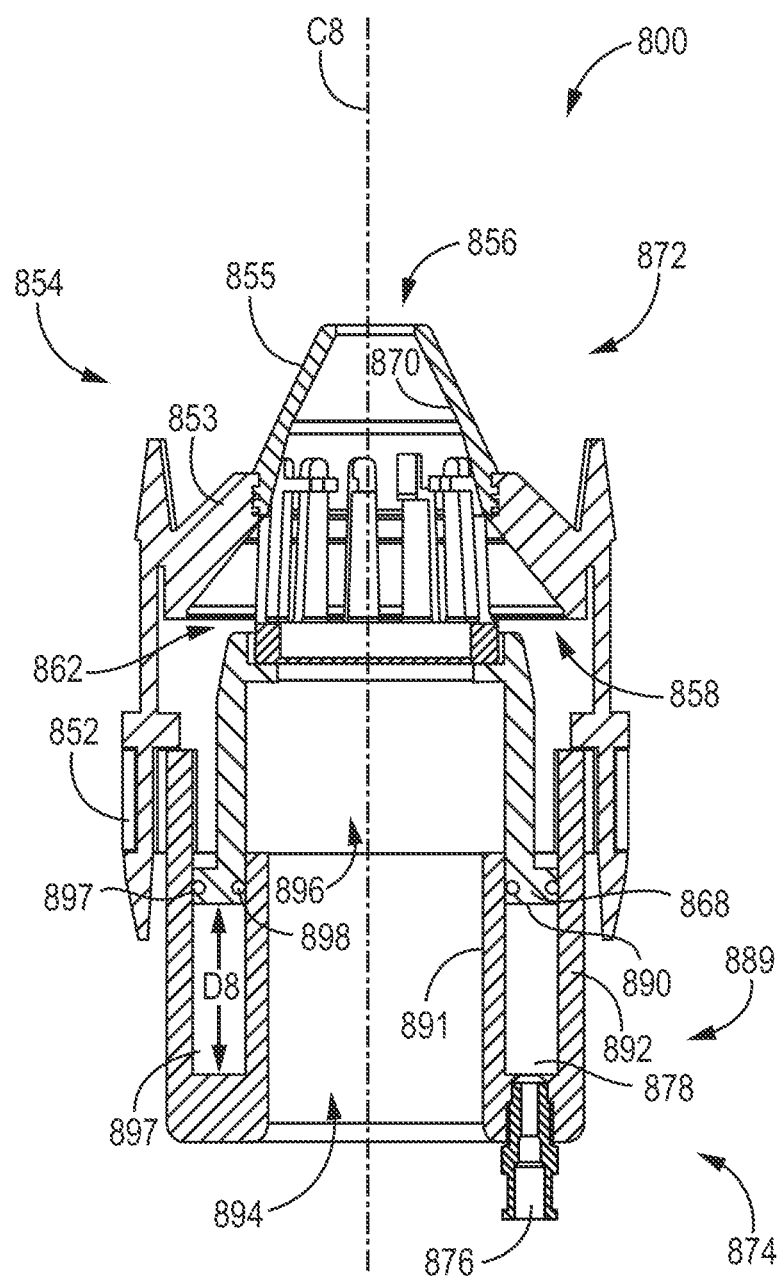
FIG. 10 is another cross-sectional illustration of the crimping device of FIG. 8.

As before, translation of the pusher 862 may precipitate contact between a prosthetic heart valve device and the internal surface 870 of the funnel 854, when the prosthetic heart valve device is positioned between the pusher 862 and the funnel 854. Funnel 854 and piston cylinder 889 are attached to housing 852. For example, FIG. 10 illustrates the crimping device 800 with the piston 868 having slidably translated over a stroke length D8 within the piston cylinder 889 as a result of, for example, a pressurized fluid supplied to the piston chamber 878 via the fluid port 876. The pusher 862 has been displaced by the sliding translation of the piston 868 such that some portion of the pusher 862 is between the distal opening 858 and the proximal opening 856 of funnel 854. In this manner, the crimping device 800 is configured to utilize the pusher 862 and the funnel 854 to crimp a prosthetic heart valve device when the prosthetic heart valve device is appropriately positioned between the pusher 862 and the proximal opening 856 of the funnel 854.

Figure 11:
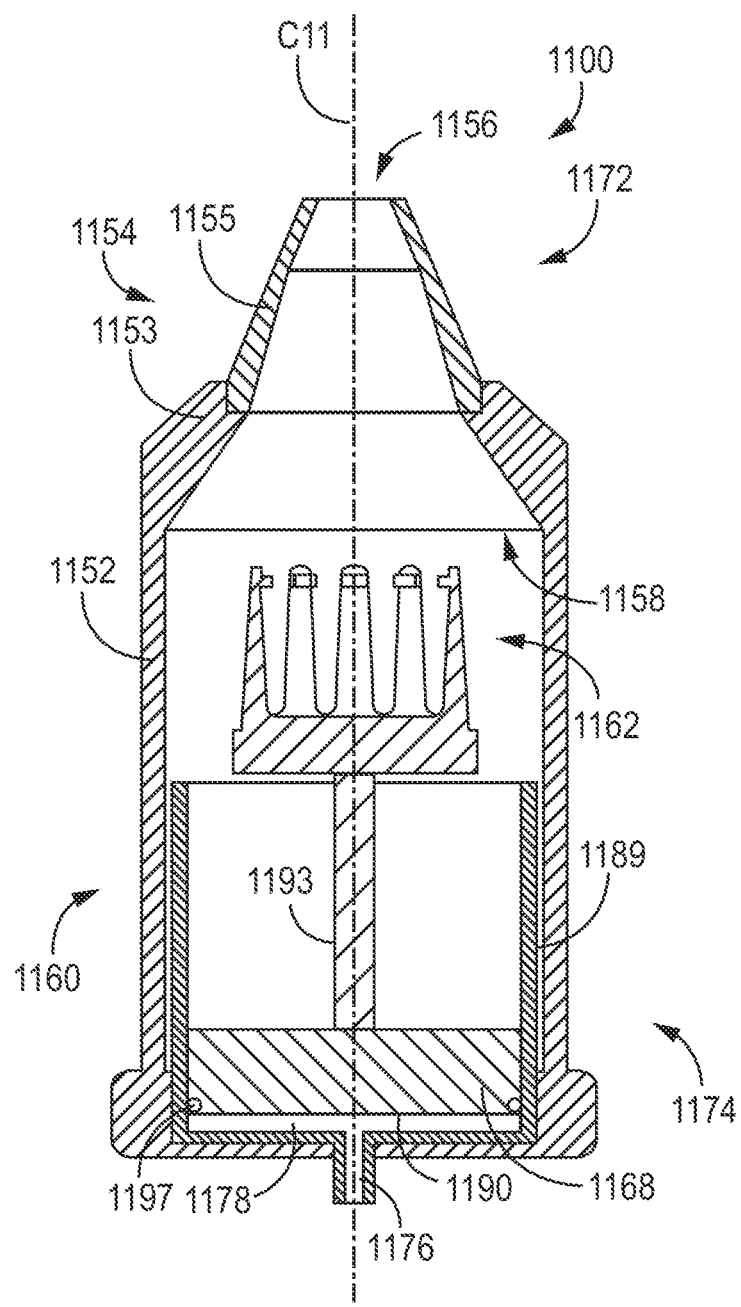
FIG. 11 is a cross-sectional illustration of an additional crimping device.

The piston of the crimping device may be a base piston connected to the pusher. The base piston and the pusher may be connected via an extending member. For example, FIG. 11 illustrates a crimping device 1100 which includes a housing 1152, a funnel 1154, a distal funnel section 1153, a proximal funnel section 1155, a proximal opening 1156, a distal opening 1158, a piston-cylinder group 1160 including a piston 1168 (configured as a base piston), piston head 1190, and piston cylinder 1189, a pusher 1162, a crimping device proximal end 1172, a crimping device distal end 1174, a fluid port 1176, piston chamber 1178, and an O-ring 1197, which may be configured similarly to and operate relative to other crimping device components in the same manner as the like-named components of the crimping device 300, crimping device 400, and/or crimping device 800. An extending member 1193 connects base piston 1168 and pusher 1162, with extending member configured such that displacement of base piston 1168 is a direction substantially parallel to longitudinal axis C11 causes extending member 1193 to displace pusher 1162 in the direction substantially parallel to longitudinal axis C11. The use of a relatively large base piston and an extender as illustrated at FIG. 11 may allow a reduction in the physical footprint of crimping device 1100, and/or may allow an increase in the force delivered to pusher 1162 for a given pressure of fluid through fluid port 1176, as compared to smaller pistons. In examples, piston 1168 has a maximum piston dimension perpendicular to longitudinal axis C11 (such as a diameter) and extending member 1193 has a maximum extending dimension perpendicular to C11 (such as another diameter), and the maximum piston diameter is greater than or equal to the maximum extending dimension.

Figure 12:
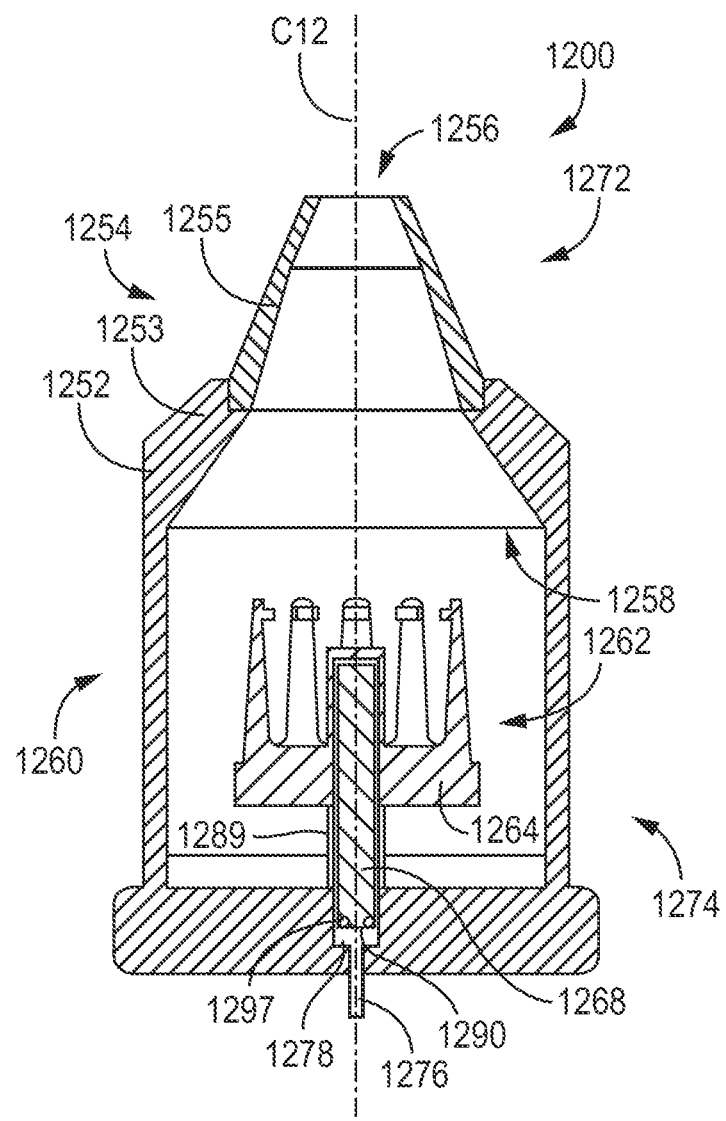
FIG. 12 is a cross-section illustration a further crimping device.

The pusher of the crimping device may be configured such that the piston inserts into the base section in order to displace the pusher toward the distal opening of the funnel. For example, FIG. 12 illustrates crimping device 1200 which includes a housing 1252, a funnel 1254, a distal funnel section 1253, a proximal funnel section 1255, a proximal opening 1256, a distal opening 1258, a piston-cylinder group 1260 including a piston 1268, piston head 1290, and piston cylinder 1289, a pusher 1262, a crimping device proximal end 1272, a crimping device distal end 1274, a fluid port 1276, piston chamber 1278, and an O-ring 1297, which may be configured similarly to and operate relative to other crimping device components in the same manner as the like-named components of the crimping device 300, crimping device 400, crimping device 800, and/or crimping device 1100. Pusher 1262 includes a base section 1264 configured to receive some portion of piston 1268. An arrangement whereby piston 1268 inserts into pusher 1262 as piston 1268 displaces pusher 1262 toward distal opening 1258 may allow a reduction in the physical footprint of crimping device 1200. Piston 1268 may be configured to engage pusher 1262 in any manner whereby piston 1268 translates pusher 1262 toward distal opening 1258 when piston 1268 translates toward distal opening 1258. For example, piston 1268 may be attached to pusher 1262 with a mechanical or other attachment means such that piston 1268 is substantially fixably attached to pusher 1262, or piston 1268 and/or pusher 1262 may be configured such that pusher 1262 may slidably translate over piston 1268.

Figure 13:
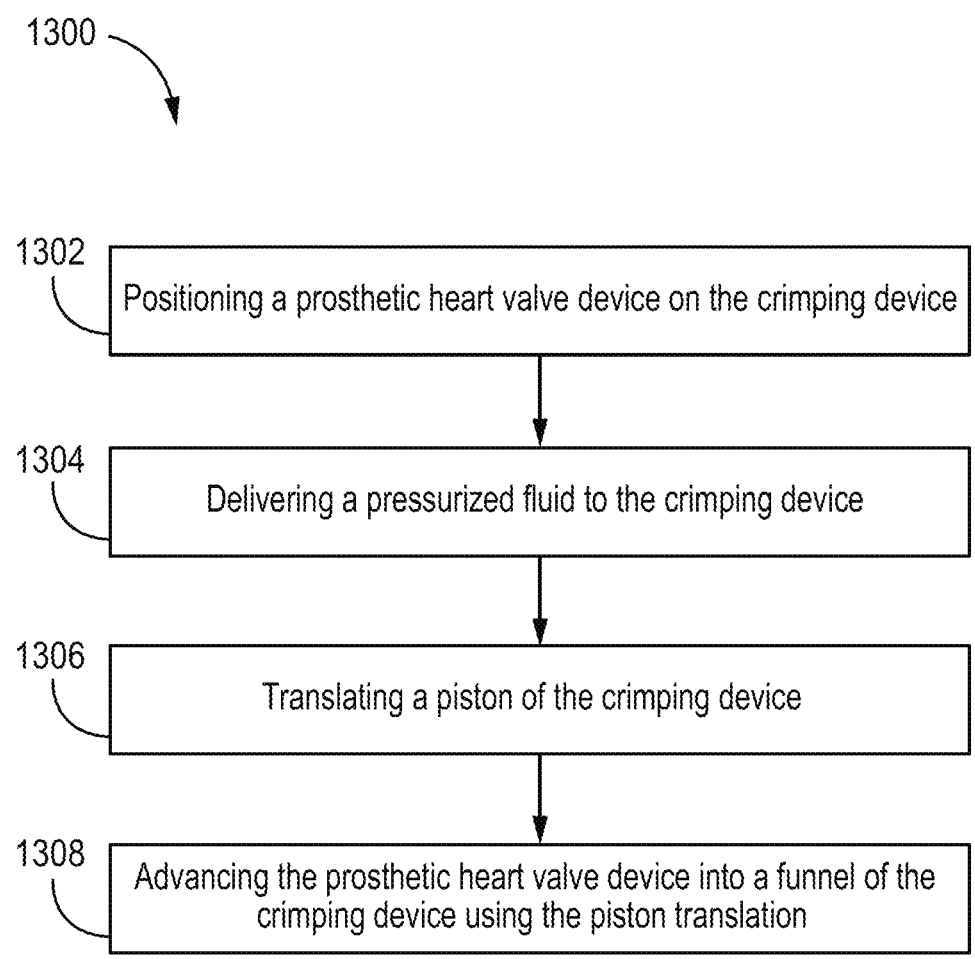
FIG. 13 is schematic flow chart for example technique for using a crimping device.

FIG. 13 illustrates a flow diagram of an example technique 1300 for crimping a prosthetic heart valve device. Although the technique is described with various reference to crimping device 300 (FIG. 3), crimping device 400 (FIG. 4, 5, 6) crimping device 800 (FIG. 8, 9, 10), crimping device 1100 (FIG. 11), and/or crimping device 1200 (FIG. 12) in other examples, the technique may be used with another crimping device. One or more steps, or all steps, may be conducted with the crimping device and the prosthetic heart valve device submerged in a solution, such as a saline solution. The crimping device and the prosthetic heart valve device may remain submerged at least until the prosthetic heart is loaded into the delivery capsule of a delivery system, such as delivery capsule 106 of delivery system 100.

The technique includes placing a prosthetic heart valve device 110, 482 between a pusher 362, 462, 862, 1162, 1262 and a distal opening 358, 458, 858 1158, 1258 of a funnel 354, 454, 854, 1154, 1254 wherein the funnel 354, 454, 854, 1154, 1254 comprises the crimping device 300, 400, 800, 1100, 1200 (1302). The pusher 362, 462, 862, 1162, 1262 may be mechanically coupled to a piston 468, 868, 1168, 1268 of a piston-cylinder group 360, 460, 860, 1160, 1260 comprising the crimping device 300, 400, 800, 1100, 1200. The pusher 362, 462, 862, 1162, 1262 may include a plurality of fingers 366, 466, 866 with one or more fingers configured to pivot toward a central axis C, C4, C8, C11, C12 of the crimping device 300, 400, 800, 1100, 1200 when a force in a direction toward central axis C, C4, C8, C11, C12 is applied to a free end of the one or more fingers. The prosthetic heart valve device 110, 482 may be positioned to at least partially cover and/or surround the free end of the one or more fingers.

The technique includes delivering a pressurized fluid to a piston cylinder 489, 889, 1189, 1289 of the crimping device 300, 400, 800, 1100, 1200 (1304). The pressurized fluid may be delivered to the piston cylinder 489, 889, 1189, 1289 via a fluid port 376, 476, 876, 1176, 1276 in fluid communication with the piston cylinder 489, 889, 1189, 1289. The pressurized fluid may exert a pressure on a piston head 490, 890, 1190, 1290 causing the piston 468, 868, 1168, 1268 to translate within piston cylinder 489, 889, 1189, 1289 in a direction from a crimping device distal end 374, 474, 874, 1174, 1274 to a crimping device proximal end 372, 472, 872, 1172, 1272. Fluid port 376, 476, 876, 1176, 1276 may include a Luer fitting. The pressurized fluid may be delivered to fluid port 376, 476, 876, 1176, 1276 from any source suitable for delivery of a pressurized fluid, such as a syringe, an inflation device, a pump, or some other device configured to contain the fluid and exert a pressure on the contained fluid.

The technique includes translating piston 468, 868, 1168, 1268 within piston cylinder 489, 889, 1189, 1289 in a direction substantially parallel to the central axis C, C4, C8, C11, C12 and from the crimping device distal end 374, 474, 874, 1174, 1274 to the crimping device proximal end 372, 472, 872, 1172, 1272 (1306). The technique includes displacing the pusher 362, 462, 862, 1162, 1262 in the direction substantially parallel to the central axis C, C4, C8, C11, C12 using the translation of piston 468, 868, 1168, 1268 within piston cylinder 489, 889, 1189, 1289.

The technique includes advancing the prosthetic heart valve device 110, 482 in the direction substantially parallel to the central axis C, C4, C8, C11, C12 and toward the distal opening 358, 458, 858, 1158, 1258 of the funnel 354, 454, 854, 1154, 1254 using the translation of the pusher 362, 462, 862, 1162, 1262 (1308). The technique may include advancing the prosthetic heart valve device 110, 482 into the funnel 354, 454, 854, 1154, 1254 (e.g., between the distal opening 358, 458, 858, 1158, 1258 and a proximal opening 356, 456, 856, 1156, 1256 of funnel 354, 454, 854, 1154, 1254). The technique may include contacting the prosthetic heart valve device 110, 482 and an internal surface 470, 870 of the funnel 354, 454, 854, 1154, 1254. The internal surface 470, 870 of the funnel 354, 454, 854, 1154, 1254 may exerts substantially uniform inward radial forces on the prosthetic heart valve device 110, 482 as the pusher 362, 462, 862, 1162, 1262 advanced the prosthetic heart valve device 110, 482 into the funnel 354, 454, 854, 1154, 1254. The technique may include compressing the prosthetic heart valve device 110, 482 using the contact between the prosthetic heart valve device 110, 482 and the internal surface 470, 870 as the pusher 362, 462, 862, 1162, 1262 advances the prosthetic heart valve device 110, 482 in the funnel 354, 454, 854, 1154, 1254.

Figure 14:
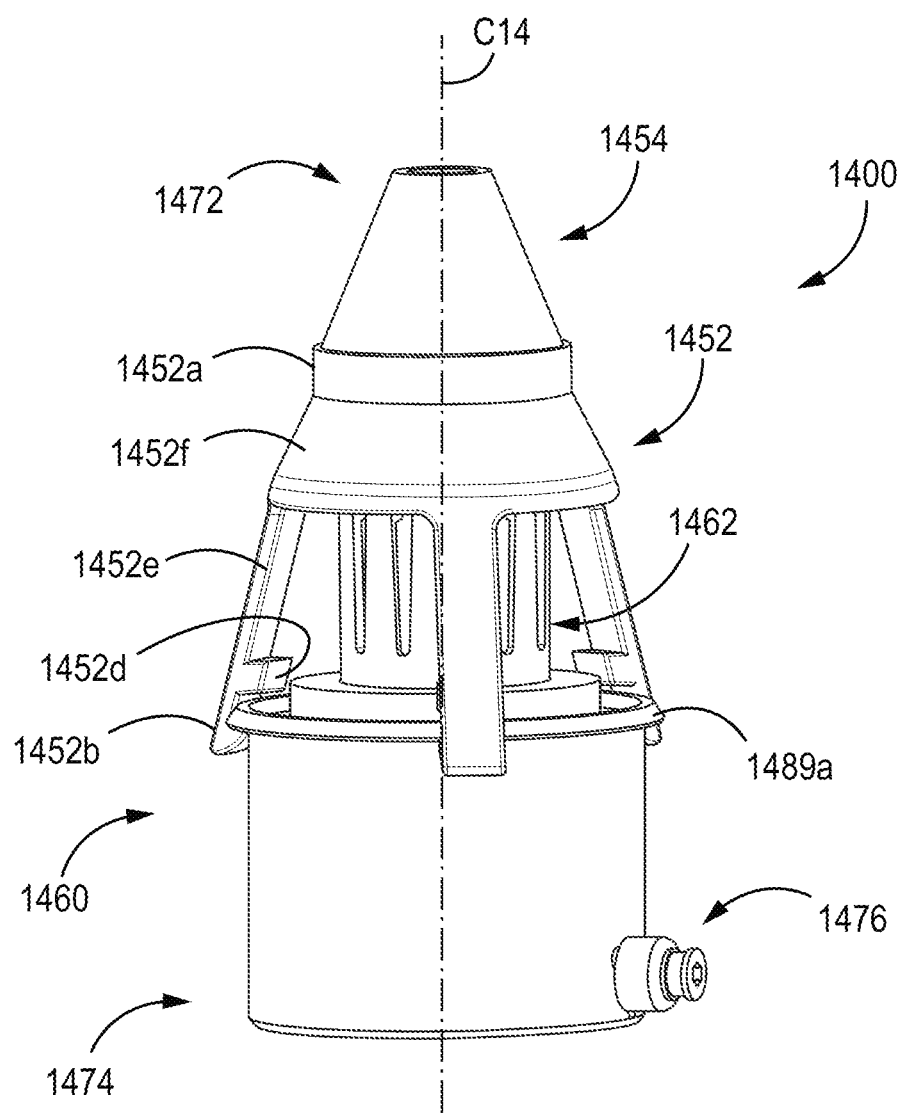
FIG. 14 is a schematic illustration of a crimping device in accordance with another embodiment hereof.
Figure 17:
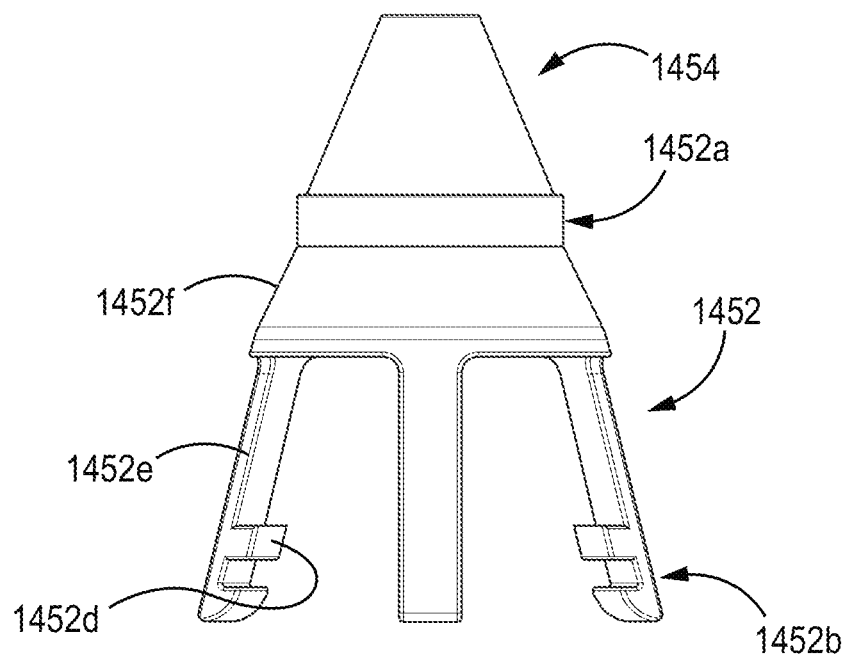
FIG. 17 is a schematic illustration of a funnel and a housing of the crimping device of FIG. 14 removed from a remainder thereof.
Figure 18:
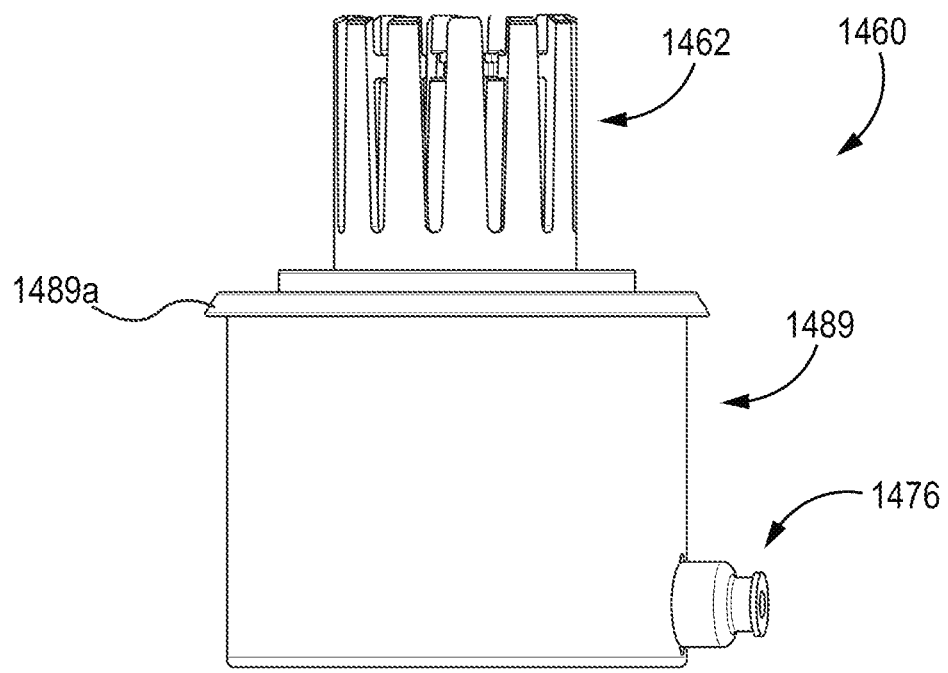
FIG. 18 is a schematic illustration of a piston-cylinder group of the crimping device of FIG. 14 removed from a remainder thereof.

FIG. 14 schematically illustrate a crimping device 1400 including a central lumen 1494 in accordance with another embodiment hereof. FIGS. 15 and 16 provide schematic cross-sections of the crimping device 1400 taken over a cutting plane perpendicular to a central axis C14, and illustrate, inter alia, the central lumen 1494 extending within the crimping device 1400. With reference to FIGS. 14-18, the crimping device 1400 includes a housing 1452, a funnel 1454, a distal funnel section 1453, a proximal funnel section 1455, a proximal opening 1456, a distal opening 1458, a piston-cylinder group 1460 including a piston 1468 (and piston head 1490) and a piston cylinder 1489, a pusher 1462, a crimping device proximal end 1472, a crimping device distal end 1474, a fluid port 1476, and O-rings 1497, 1498, which may be configured similarly to and operate relative to other crimping device components in the same manner as the like-named components of the crimping devices 300, 400, 800. Likewise, the components of the crimping device 1400 discussed below may be present in the crimping devices 300, 400, 800 and may be configured similarly to and operate relative to other crimping device components in the same manner as discussed for the crimping device 1400.

As illustrated by FIGS. 15 and 16, the central lumen 1494 may extend through the piston-cylinder group 1460 and at least partially surround the central axis C14. The central axis C14 intersects the distal opening 1458 and the proximal opening 1456 of the funnel 1454. In an embodiment that is similar to that shown in FIGS. 8-10, the central lumen 1494 may be in fluid communication with a piston opening and a pusher opening, such that the central lumen 1494, the piston opening, and the pusher opening substantially form a single passage accessible from both the crimping device proximal end 1472 and the crimping device distal end 1474. In some configurations, such as the transfemoral delivery system, it may be advantageous to pass the delivery system through the central lumen in order to attach a prosthetic heart valve device to a delivery system in an opposite orientation to other configurations, such as the transapical deliver system. This may allow for different directions of approach to the native anatomy and different deployment orientations for the clinician during use.

The central lumen 1494 surrounds longitudinal axis C14 and extends through the piston cylinder 1489, such that the piston cylinder 1489 is configured to substantially surround some portion of the central lumen 1494. The piston cylinder 1489 may include an interior wall 1491 and an exterior wall 1492 in which the interior wall 1491 is disposed between the exterior wall 1492 and the central axis C14. The interior wall 1491 may define an inner wall of the central lumen 1494. The interior wall 1491 and/or the exterior wall 1492 may define any cross-section perpendicular to the central axis C14. For example, the interior wall 1491 and/or the exterior wall 1492 may define an elliptical (including circular) cross-section, an oval-shaped cross-section, a regular or irregular polygonal cross-section, or some other cross-sectional shape which surrounds at least some portion of the central axis C14.

The piston 1468 is configured to translate within the piston cylinder 1489 and form a piston chamber bounded at least in part by the piston cylinder 1489 and a piston head 1490 of the piston 1468. The O-ring 1497 extends around an exterior-facing perimeter of the piston 1468 to provide a fluid barrier between the piston chamber formed and any clearances between the piston 1468 and the exterior wall 1492. The O-ring 1498 extends around an interior-facing perimeter of the piston 1468 to provide a fluid barrier between the piston chamber formed and any clearances between the piston 1468 and the interior wall 1491. A pressurized fluid delivered via a fluid port 1476 may act on the piston head 1490 and cause the piston 1468 to translate in a direction from the crimping device distal end 1474 to the crimping device proximal end 1472. In the embodiment of FIGS. 14-16 and 18, the fluid port 1476 laterally extends through the exterior wall 1492 of the piston cylinder 1489, or in other words from a side of the crimping device 1400, and may comprise a Luer fitting or other type of suitable fitting for the delivery of a pressurized fluid.

The piston 1468 is mechanically coupled to the pusher 1462, such that a hydraulically-driven displacement of the piston 1468 causes pusher 1462 to translate in a direction that is substantially parallel to the central axis C14. In order to allow access throughout the crimping device 1400 (either proximally or distally), the pusher 1462 may include a pusher opening that extends through the pusher 1462 and at least partially surrounds central axis C14. As previously noted, any such pusher opening would be in fluid communication with the central lumen 1494 of the piston cylinder 1489.

As described in detail above with respect to prior embodiments, translation of the pusher 1462 may precipitate contact between a prosthetic heart valve device and an internal surface of the funnel 1454, when the prosthetic heart valve device is positioned between the pusher 1462 and the funnel 1454. In the embodiment depicted in FIGS. 14-18, a proximal end 1452a of the housing 1452 is attached to the funnel 1454 via a threadable connection 1452c, and a distal end 1452b of the housing 1452 is attached to the piston cylinder 1489. More particularly, the distal end 1452b of the housing 1452 includes a plurality of retention clips 1452d that are configured to provide a snap-fit engagement with a circumferential ledge 1489a of the piston cylinder 1489. In an embodiment, and as shown in FIGS. 14-16 and 18, a circumferential ledge 1489a may extend about a perimeter of a proximal end of the piston cylinder 1489 to provide ease and ready attachment thereto by the plurality of retention clips 1452d no matter the orientation of the housing 1452 relative to the piston cylinder 1489. In the embodiment of FIGS. 14-18, each of the retention clips 1452d forms a distal end of a respective arm 1452e of the housing 1452. In the embodiment of FIGS. 14-18, the housing 1452 is shown with three arms 1452e distally extending from a proximal segment 1452f of the housing 1452, and each of the arms 1452e includes a respective retention clip 1452d. The exact number of arms and retention clips may vary without departing from the scope hereof.

In an embodiment, a housing 1452 with a funnel 1454 attached thereto are detached from a piston-cylinder group 1460 to permit a prosthetic heart valve device to be positioned between the pusher 1462 and the funnel 1454 as described above. The housing 1452 and the funnel 1454 are then snapped to the piston cylinder 1489 through engagement between the retention clips 1452*d* of the housing 1452 and the ledge 1489*a* of the piston cylinder 1489. The piston 1468 of the crimping device 1400 is then slidably translated over a stroke length within the piston cylinder 1489 as a result of, for example, a pressurized fluid being supplied to the piston chamber via the fluid port 1476. The pusher 1462 having been displaced by the sliding translation of the piston 1468 such that some portion of the pusher 1462 is between the distal opening 1458 and the proximal opening 1456 of funnel 1454. In this manner, the crimping device 1400 is configured to utilize the pusher 1462 and the funnel 1454 to crimp a prosthetic heart valve device when the prosthetic heart valve device is appropriately positioned between the pusher 1462 and the funnel 1454.

Various examples have been described. These and other examples are within the scope of the following claims.

What is claimed is:

1. A method comprising:
   placing a prosthetic heart valve device in a crimping device between a pusher of the crimping device and a distal opening of a funnel of the crimping device;
   delivering a pressurized fluid to a piston cylinder of the crimping device;
   translating a piston within the piston cylinder in a direction substantially parallel to a central axis using the supplied pressurized fluid, wherein the central axis intersects the distal opening of the funnel and a proximal opening of the funnel, and wherein the distal opening is between the proximal opening and the piston cylinder;
   displacing the pusher in the direction substantially parallel to the central axis using the translation of the piston; and
   advancing the prosthetic heart valve device in the direction along the central axis and toward the distal opening of the funnel using the displacement of the pusher,
   wherein delivering the pressurized fluid to the piston cylinder comprises delivering the pressurized fluid to a piston chamber defined by a head of the piston and a wall of the piston cylinder, and
   wherein translating the piston within the piston cylinder comprises a proximal end of the piston extending proximally beyond a proximal end of the piston cylinder.

2. The method of claim 1 further comprising:
   advancing the prosthetic heart valve device into the funnel;
   contacting the prosthetic heart valve device against an interior surface of the funnel; and
   compressing the prosthetic heart valve device using the contact between the prosthetic heart valve device and the interior surface of the funnel.

3. The method of claim 2, further comprising flexing or pivoting a portion of the pusher inwardly toward the central axis using the compressing of the prosthetic heart valve device.

4. The method of claim 3, wherein the pusher comprises a pusher base and a plurality of fingers extending from the pusher base, wherein the placing the prosthetic heart valve device in the crimping device comprises placing a portion of the prosthetic heart valve device around the plurality of fingers.

5. The method of claim 4, wherein flexing or pivoting a portion of the pusher inwardly comprises flexing or pivoting the plurality of fingers inwardly.

6. The method of claim 1, wherein:
   placing the prosthetic heart valve device in the crimping device further comprises placing the prosthetic heart valve device in a housing of the crimping device between the pusher and the funnel attached to the housing; and
   delivering the pressurized fluid to the piston cylinder comprises delivering the pressurized fluid to the piston cylinder attached to the housing surrounding the piston cylinder.

7. The method of claim 6, wherein the wall of the piston cylinder comprises an interior wall of the piston cylinder that surrounds the piston.

8. The method of claim 1, wherein the wall of the cylinder comprises an interior wall surrounding a central lumen and an exterior wall surrounding the interior wall, wherein the piston is disposed between the interior wall and the exterior wall.

9. The method of claim 8, wherein delivering pressurized fluid to the piston cylinder comprises delivering the pressurized fluid to a piston chamber defined by a head of the piston, the interior wall of the piston cylinder, the exterior wall of the piston cylinder, and a distal wall of the piston cylinder.

10. A method comprising:
    placing a prosthetic heart valve device in a housing of a crimping device between a pusher of the crimping device and a distal opening of a funnel attached to the housing of the crimping device;
    translating a piston of the crimping device within a piston cylinder attached to the housing in a direction substantially parallel to a central axis, wherein the central axis intersects the distal opening of the funnel and a proximal opening of the funnel, and wherein the distal opening is between the proximal opening and the piston cylinder;
    displacing the pusher in the direction substantially parallel to the central axis using the translation of the piston; and
    advancing the prosthetic heart valve device in the direction along the central axis and into the funnel;
    compressing the prosthetic heart valve device by contacting the prosthetic heart valve device against an interior surface of the funnel; and
    flexing or pivoting a portion of the pusher inwardly toward the central axis using the compressing of the prosthetic heart valve device.

11. The method of claim 10, wherein the pusher comprises a pusher base and a plurality of fingers extending from the pusher base, wherein the placing the prosthetic heart valve device in the crimping device comprises placing a portion of the prosthetic heart valve device around the plurality of fingers.

12. The method of claim 11, wherein flexing or pivoting a portion of the pusher inwardly comprises flexing or pivoting the plurality of fingers inwardly.

13. The method of claim 10, wherein translating the piston comprises delivering a pressurized fluid to the piston cylinder of the crimping device.

14. The method of claim 13, wherein delivering the pressurized fluid to the piston cylinder comprises delivering the pressurized fluid to the piston cylinder attached to the housing surrounding the piston cylinder.

15. The method of claim 14, wherein:
    delivering the pressurized fluid to the piston cylinder comprises delivering the pressurized fluid to a piston chamber defined by a head of the piston and an interior wall of the piston cylinder; and translating the piston within the piston cylinder comprises a proximal end of the piston extending beyond a proximal end of the piston cylinder.

16. The method of claim 14, wherein delivering pressurized fluid to the piston cylinder comprises delivering the pressurized fluid to an annular cylinder including an interior wall surrounding a central lumen and an exterior wall surrounding the interior wall, wherein the piston is disposed between the interior wall and the exterior wall.

17. The method of claim 16, wherein delivering pressurized fluid to the piston cylinder comprises delivering the pressurized fluid to a piston chamber defined by a head of the piston, the interior wall of the piston cylinder, the exterior wall of the piston cylinder, and a distal wall of the piston cylinder.

\* \* \* \* \*